US006974825B1

(12) United States Patent
Pelcman et al.

(10) Patent No.: US 6,974,825 B1
(45) Date of Patent: *Dec. 13, 2005

(54) COMPOUNDS WITH ANALGESIC EFFECT

(75) Inventors: Benjamin Pelcman, Stockholm (SE); Edward Roberts, St. Lazare de Vaudreuil (CA)

(73) Assignee: AstraZeneca Canada Inc., Mississauga (CA)

( * ) Notice: Subject to any disclaimer, the term of this patent is extended or adjusted under 35 U.S.C. 154(b) by 37 days.

This patent is subject to a terminal disclaimer.

(21) Appl. No.: 10/628,309

(22) Filed: Jul. 29, 2003

Related U.S. Application Data

(60) Continuation of application No. 10/121,683, filed on Apr. 15, 2002, now Pat. No. 6,710,179, which is a division of application No. 09/645,565, filed on Aug. 25, 2000, now Pat. No. 6,399,635, which is a division of application No. 09/029,468, filed as application No. PCT/SE97/02051 on Dec. 9, 1997, now Pat. No. 6,153,626.

(30) Foreign Application Priority Data

Dec. 20, 1996 (SE) .................................. 9604786

(51) Int. Cl.[7] .................. A61K 31/4468; A61K 31/445; C07D 211/58; A61P 1/00; A61P 25/00
(52) U.S. Cl. ...................... 514/329; 514/426; 546/223; 546/224; 548/557
(58) Field of Search ................................ 546/223, 224; 548/557; 514/329, 426

(56) References Cited

U.S. PATENT DOCUMENTS

| 4,091,096 | A | 5/1978 | Beck et al. .................. 514/157 |
| 4,126,689 | A | 11/1978 | Sanczuk et al. ............. 514/329 |
| 4,460,586 | A | 7/1984 | Berthold ...................... 424/250 |
| 4,680,296 | A | 7/1987 | Manoury et al. ............ 514/259 |
| 5,118,693 | A | 6/1992 | Toth et al. ................... 514/327 |
| 5,132,303 | A | 7/1992 | Toth et al. ................... 514/278 |
| 5,132,309 | A | 7/1992 | Toth et al. ................... 514/278 |
| 5,854,245 | A | 12/1998 | Duggan et al. .............. 514/250 |
| 6,153,626 | A | 11/2000 | Pelcman et al. ............. 514/329 |
| 6,399,635 | B1 | 6/2002 | Pelcman et al. ............. 514/329 |
| 6,436,959 | B1 | 8/2002 | Carson et al. ............... 514/326 |

FOREIGN PATENT DOCUMENTS

| DE | 28 22 465 | 11/1978 | ......... C07D 471/04 |
| HU | 206 677 | 8/1989 | ......... C07D 211/22 |
| WO | WO 98/28270 | 7/1998 | ......... C07D 211/56 |
| WO | WO 99/33806 | 7/1999 | ......... C07D 211/58 |
| WO | WO 99/45925 | 9/1999 | ........ A61K 31/435 |

OTHER PUBLICATIONS

Adachi, et al., "Aminohaloborane in Organic Synthesis. IX. Exclusive Ortho Acylation Reacfdtion of N-Monoaminoalkylanilines," XP002277753, Database Chemabs Online, Accession No. 1987:49715, *Chemical & Pharmaceutical Bulletin* 33(5):1826-1835 (1985).

Burkartsmaier, et al., "Potential Analgesics, IX: Synthesis and Pharmacological Test of Substituted N-(Piperidin-4-yl) Anthranilic Acid Derivatives," XP002277757, Database Chemabs Online, Accession No. 1979:54780, *Archiv. der Pharmazie* 311(10):843-848 (1978).

Deruiter, et al., "Investigation of the Synthesis and Analgesic Activity of 1-Substituted 4-(Propananilido) Perhydroazepines," XP002277751, Database Chemabs Online, Accession No. 1992:612296, *J. Heterocyclic Chem.* 29(4):779-786 (1992).

Ferrand, et al., "Synthesis of new 1,2,3-triazin-4-Ones as Potential Antidepressants," XP002277752, Database Chemabs Online, Accession No. 1988:150431, *Eur. J. Medicinal Chem.* 22(4):337-345 (1987).

Obase, et al., "New Antihypertensive Agents. III. Synthesis and Antihypertensive Activity of Some Arylalkyl Piperidines Carrying a Heterocycle at the 4-Position," XP002277758, Database Chemabs Online, Accession No. 1984:120835, *Chemical & Pharmaceutical Bulletin* 31(9): 3186-3197 (1983).

Sugasawa, et al., "1-Azacycloalkyl-1,4-Benzodiazepin-2-Ones with Antianxiety-Antidepressant Actions," XP002277755, Database Chemabs Online, Accession No. 1985:437458, *J. Medicinal Chem.* 28(6):699-707 (1985).

Takai, et al., "Synthesis and Pharmacological Evaluations of Piperidine Derivatives with Various Heterocyclic Rings at the 4-Position," XP002277754, Database Chemabs Online, Accession No. 1985:578235, *Chemical & Pharmaceutical Bulletin* 33(3):1104-1115 (1985).

(Continued)

*Primary Examiner*—Evelyn Mei Huang
(74) *Attorney, Agent, or Firm*—Michael A. Sanzo; Fitch, Even, Tabin & Flannery

(57) ABSTRACT

Compounds of general formula (I)

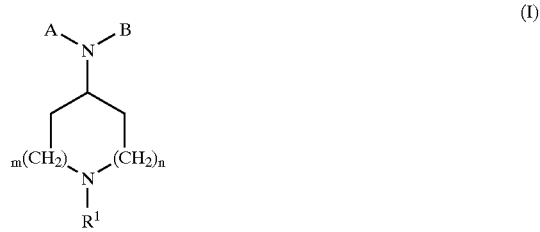

wherein m is 0 or 1, and n is 1 or 2;
are disclosed and claimed in the present application, as well as their pharmaceutically acceptable salts, pharmaceutical compositions comprising the novel compounds and their use in therapy, in particular in the management of pain.

73 Claims, No Drawings

OTHER PUBLICATIONS

Wang, et al., "Opioid .Delta. Receptor Irreversible Inhibitors. 2. Synthesis of Isothiocyanate Derivatives of Carfentanil and 4-(Methoxymethyl)Fentanyl," XP002277750, Database Chemabs Online, Accession No. 1995:857886, *Chinese Chemical Letters 6(9)*:763-764 (1995).

Zhu, et al., "Studies on Potent Analgesics. I. Synthesis and Analgesic Activity of Fentanyl Derivatives," XP002277756, Database Chemabs Online, Accession No. 1981:550311, *Yaoxue Xuebao 16(3)*:199-210 (1981).

Bilsky, et al., SNC 80, A Selective, Nonpeptidic and Systemically Active Opioid Delta Agonist, *J. Pharmacol. Experi. Ther. 273*:359-366 (1995).

Enein, et al., Abstract #159379n, "Synthesis of Some 4-Substituted Amino-1-Methyl Piperidines Structurally Related to Antihistaminics," *Chem. Abstr.*, vol. 78, No. 25, p. 396 (1973).

Laskowska, Abstr. #105299e, "1-Methyl-4-[N-phenyl-N-(2-thienyl)amino]piperidine," *Chem. Abstr.*, vol. 81, No. 17, p. 510 (1975).

Podlogar, et al., "Synthesis and Evaluation of 4-(N,N-Diarylamino)piperidines with High Selectivity to the 8-Opioid Receptor: A Combined 3D-QSAR and Ligand Docking Study," *Drug Design and Discovery,* 34-50 (2000).

Sarges, et al., "Neuroleptic Activity of Chiral trans-Hexahydro-γ-Carbolines," *J. Med. Chem. 29*:8-19 (1986).

Takemori, et al., "Selective Natrexone-Derived Opioid Receptor Antagonists," *Annu. Ref. Pharmacol. Toxicol. 32*: 239-269 (1992).

Abstract for DE 28 22 465, Reference AK1 above.

Abstract for HU 206 677, Reference AH2 below.

English language abstract for HU 206 677, Reference AH2 above.

COMPOUNDS WITH ANALGESIC EFFECT

CROSS REFERENCE TO RELATED APPLICATIONS

The present application is a continuation of U.S. application Ser. No. 10/121,683 (now U.S. Pat. No. 6,710,179), filed on Apr. 15, 2002 which is a division of U.S. application Ser. No. 09/645,565, filed on Aug. 25, 2000 (now U.S. Pat. No. 6,399,635). The '565 application is a division of U.S. application Ser. No. 09/029,468, filed on Mar. 3, 1998 (now U.S. Pat. No. 6,153,626). The '468 application represented U.S. national stage of international application PCT/SE97/02051, which had an international filing date of Dec. 9, 1997, and which was published in English under PCT Article 21(2) on Jul. 2, 1998. The international application claims priority to Swedish application 9604786-5, filed on Dec. 20, 1996.

FIELD OF THE INVENTION

The present invention is related to novel nitrogen ring compounds, to a process for their preparation, their use and pharmaceutical compositions comprising the novel compounds. The novel compounds are useful in therapy, and in particular for the treatment of pain.

BACKGROUND AND PRIOR ART

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors ($\mu$, $\delta$ and $\kappa$) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. Some non-peptidic δ antagonists have been available for some time (see Takemori and Portoghese, 1992, Ann. Rev. Pharmacol. Tox., 32: 239–269, for review). These compounds, e.g. naltrindole, suffer from rather poor (i.e., <10-fold) selectivity for the δ receptor vs. $\mu$ receptor binding and exhibit no analgesic activity, a fact which underscores the need for the development of highly selective non-peptidic δ ligands.

Thus, the problem underlying the present invention was to find new analgesics having improved analgesic effects, but also with an improved side-effect profile over current $\mu$ agonists and potential oral efficacy.

Analgesics that have been identified and are existing in the prior art have many disadvantages in that they suffer from poor pharmacokinetics and are not analgesic when administered by systemic routes. Also, it has been documented that preferred compounds, described within the prior art, show significant convulsive effects when administered systemically.

The problem mentioned above has been solved by developing novel compounds which possess a piperidine ring, which may be a 5-membered, a 6-membered or a 7-membered nitrogen ring, as will be described below.

OUTLINE OF THE INVENTION

The novel compounds according to the present invention are defined by the general formula (I)

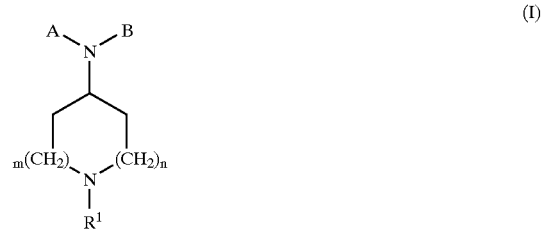

wherein
m is 0 or 1;
n is 1 or 2;
$R^1$ is selected from
hydrogen;
a branched or straight $C_1$–$C_6$ alkyl;
$C_3$–$C_8$ cycloalkyl;
$C_4$–$C_8$(alkyl-cycloalkyl) wherein alkyl is $C_1$–$C_2$ alkyl and cycloalkyl is $C_3$–$C_6$ cycloalkyl; benzyl;

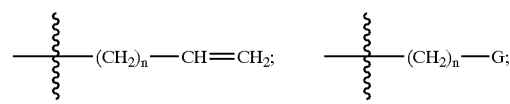

where G is a hydroaromatic or a heteroaromatic group having 5 or 6 atoms, and where the heteroatoms are selected from O, S and N; and

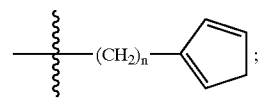

and wherein n=0 or 1;
$C_6$–$C_{10}$ aryl; or heteroaryl having from 5 to 10 atoms selected from any of C, S, N and O; wherein the aryl and heteroaryl may optionally and independently be substituted by 1 or 2 substituents independently selected from any of hydrogen, $CH_3$, $(CH_2)_pCF_3$, halogen, $CONR^5R^4$, $COOR^5$, $COR^5$, $(CH_2)_pNR^5R^4$, $(CH_2)_pCH_3(CH_2)_p$ $SOR^5R^4$, $(CH_2)_pSO_2R^5$ and $(CH_2)_pSO_2NR^5$, wherein $R^4$ and $R^5$ is each and independently as defined for $R^1$ above and p is 0, 1 or 2;
($C_1$–$C_2$ alkyl)-($C_6$–$C_{10}$ aryl); or ($C_1$–$C_2$ alkyl)heteroaryl, the heteroaryl moieties having from 5 to 10 atoms selected from any of C, S, N and O, and where the aryl or heteroaryl may optionally and independently be substituted by 1 or 2 substituents independently selected from any of hydrogen, $CH_3$, $CONR^5R^4$, $COOR^5$, $COR^5$, $(CH_2)_q$ $NR^5R^4$, $(CH_2)_qCH_3(CH_2)_qSOR^5R^4$, $(CH_2)_q$ $SO_2R^5$, $(CH_2)_qSO_2NR^5$, and $(CH_2)_qOR^4$, wherein $R^4$ and $R^5$ is each and independently as defined for $R^1$ above and q is 0, 1 or 2;

A is

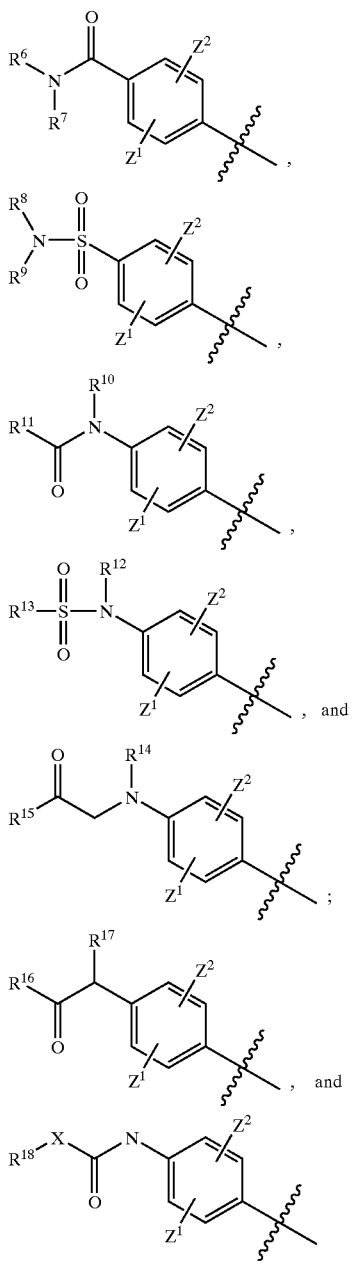

wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is each and independently as defined for $R^1$ above and wherein the phenyl ring of each A substituent may be optionally and independently substituted by 1 or 2 substituents $Z^1$ and $Z^2$ which are each and independently selected from hydrogen, $CH_3$, $(CH_2)_rCF_3$, halogen, $CONR^2R^3$, $CO_2R^2$, $COR^2$, $(CH_2)_rNR^2R^3$, $(CH_2)_rCH_3$ $(CH_2)_r SOR^2$, $(CH_2)_rSO_2R^2$ and $(CH_2)_rSO_2NR^2R^3$ wherein $R^2$ and $R^3$ is each and independently as defined for $R^1$ above and wherein r is 0, 1, or 2; X is O, S or $NR^{19}$ where $R^{19}$ is as defined for $R^1$, B is a substituted or unsubstituted aromatic, heteroaromatic, hydroaromatic or heterohydroaromatic moiety having from 5 to 10 atoms selected from any of C, S, N and O, optionally and independently substituted by 1 or 2 substituents independently selected from hydrogen, $CH_3$, $(CH_2)_rCF_3$, halogen, $(CH_2)_rCONR^5R^4$, $(CH_2)_rNR^5R^4$, $(CH_2)_rCOR^5$, $(CH_2)_rCOOR^5$, $OR^5$, $(CH_2)_rSOR^5$, $(CH_2)_rSO_2R^1$, and $(CH_2)_rSO_2NR^5R^4$, wherein $R^4$ and $R^5$ is each and independently as defined for $R^1$ above, and t is 0, 1, 2 or 3;

Within the scope of the invention are also pharmaceutically acceptable salts of the compounds of the formula (I), as well as isomers, hydrates, isoforms and prodrugs thereof.

Preferred compounds according to the invention are compounds of the formula (I) wherein $R^1$ is selected from benzyl;

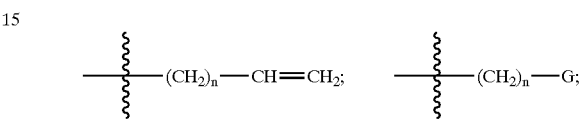

where G is a hydroaromatic or a heteroaromatic group having 5 or 6 atoms, and where the heteroatoms are selected from O, S and N; and

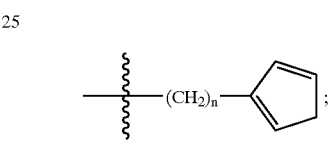

and wherein n=0 or 1;

A is selected from anyone of

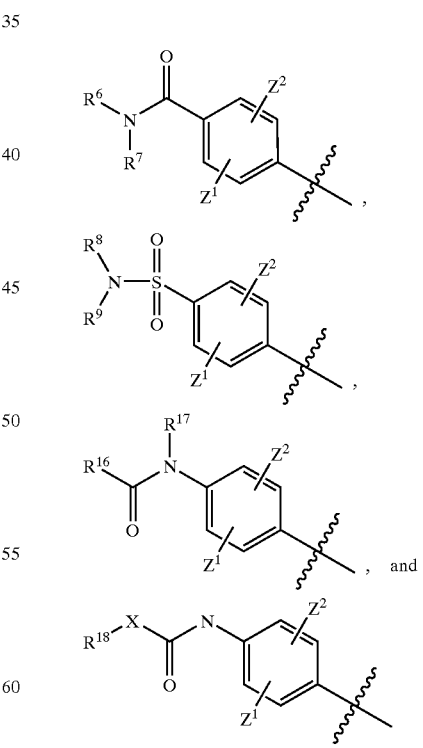

wherein $R^6$, $R^7$, $R^8$, $R^9$, $R^{16}$, $R^{17}$ and $R^{18}$ is each and independently as defined for $R^1$ above; and $Z^1$, $Z^2$ and X is each and independently as defined above;

B is selected from phenyl, naphthyl, indolyl, benzofuranyl, dihydrobenzofuranyl, benzothiophenyl, pyrryl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, tetrahydrofuranyl, pyrrolidinyl, and indazolinyl, each optionally and independently substituted by 1 or 2 substituents independently selected from hydrogen, $CH_3$, $CF_3$, halogen, $-(CH_2)_tCONR^5R^4$, $-(CH_2)_tNR^5R^4$, $-(CH_2)_tCOR^5$, $-(CH_2)_tCO_2R^5$, and $-OR^5$, wherein t is 0 or 1, and wherein $R^4$ and $R^5$ are as defined above.

Especially preferred compounds are compounds of the formula (I) wherein
$R^1$ is ($C_1$–$C_2$ alkyl)phenyl and hydrogen;
A is

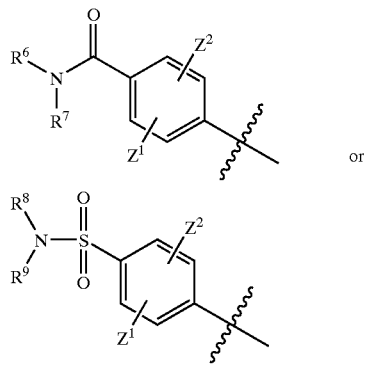

wherein $R^6$, $R^7$, $R^8$, $R^9$, is each an ethylene group; and $Z^1$ and $Z^2$, are as defined above;
B is phenyl or naphtalene; and
m and n is each 1, or m is 1 and n is 0.

The substituents A and B respectively, may optionally be substituted at any position of the ring.

By "halogen" we mean chloro, fluoro, bromo and iodo.

By "aryl" we mean an aromatic ring having from 6 to 10 carbon atoms, such as phenyl and naphtyl.

By "heteroaryl" we mean an aromatic ring in which one or more of the from 5–10 atoms in the ring are elements other than carbon, such as N, S and O.

By "hydroaromatic" we mean a partly or fully saturated aromatic ring structure having from 5–10 carbon atoms in the ring.

By "heterohydroaromatic" we mean a partly or fully saturated aromatic ring structure in which one or more of the from 5–10 atoms in the ring are elements other than carbon, such as N, S and O.

By "isomers" we mean compounds of the formula (I), which differ by the position of their functional group and/or orientation. By "orientation" we mean stereoisomers, diastereoisomers, regioisomers and enantiomers.

By "isoforms" we mean compounds of the formula (I) which differ by their crystal lattice, such as crystalline compound and amorphous compounds.

By "prodrug" we mean pharmacologically acceptable derivatives, e.g. esters and amides, such that the resulting biotransformation product of the derivative is the active drug. The reference by Goodman and Gilmans, The Pharmacological basis of Therapeutics, 8th ed., McGraw-Hill, Int. Ed. 1992, "Biotransformation of Drugs," p. 13–15, describing prodrugs generally, is hereby incorporated.

The novel compounds of the present invention are useful in therapy, especially for the treatment of various pain conditions such as chromic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, urinary incontinence, various mental illnesses, cough, lung oedema, various gastrointestinal disorders, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (eg. Amnesia, analgesia, muscle relaxation and sedation). Included in this combination are inhaled anaesthetics, hypnotica, anxiolytics, neuromuscular blockers and opioids.

The compounds of the present invention in isotopically labelled form are useful as a diagnostic agent.

Also within the scope of the invention is the use of any of the compounds according to the formula (I) above, for the manufacture of a medicament for the treatment of any of the conditions discussed above.

A further aspect of the invention is a method for the treatment of a subject suffering from any of the conditions discussed above, whereby an effective amount of a compound according to the formula (I) above, is administered to a patient in need of such treatment.

Methods of Preparation

Compounds of the formula (I), as described above, may be obtained by the arylation of an amine of formula (II)

wherein $R^1$, m and n are as defined in formula (I) above, and W is A or B as defined in formula (I) above, by an arylating agent of formula (I)

wherein W is A or B as defined in formula (I) above, and Z is a suitable substituent, i.e. a reactive component suitable to be used in the defined process, which will be appreciated by a person skilled in the art, preferably halogen, triflate ($CF_3SO_3$—), mesylate ($CH_3SO_3$—), tosylate ($CH_3(C_6H_4)SO_3$—), tributyltin, triacetoxylead, diarylbismuth, borate ($B(OH)_2$), cuprate or other such group known in the art. The arylation may be catalyzed by metals, preferably Cu, Ni, Pd or suitable salts, complexes, oxides or hydroxides thereof. The 4-aminopiperidine of formula (II) above may be converted completely or partially to its corresponding anion by treatment with bases, preferably triethylamine, 4-dimethylaminopyridine, $K_2CO_3$, NaOH, NaH, lithium diisopropylamide, sodium tert-butoxide or the like, prior or during the arylation process. The reaction may be performed in the presence of complexing reagents, preferably triphenylphosphine, triphenylarsine, dibenzylideneacetone, 2,2'-bis(diphenylphosphino)-1,1'-binaphtyl, 1,1'-bis(diphenylphosphino)ferrocene, oxygen or other such compounds known in the art. The reaction may optionally be performed in the presence of one or more solvents such as toluene, dichloromethane, tetrahydrofuran, dimethylformamide, dioxane, acetonitrile or dimethylsulfoxide, or in solvent mixtures.

$R^1$ and the substituents on A and B of compound (I) as defined above, may be modified after or during the preparation of (I) from (II) and (III) by methods known in the art, for example reduction, oxidation and alkylation.

The amine of formula (II) may be prepared by reductive amination of a ketone of the formula (IV)

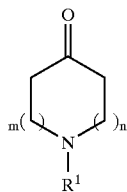
(IV)

wherein $R^1$, $R^2$, $R^3$, m and n are as defined in formula (I) above, with a substituted arylamine (V)

(V)

wherein W is as defined in formula (II) above.

The reductive amination may be performed in a one or a two stage process involving a Brønstedt or a Lewis acid and a reducing agent. Suitable acids are sulphuric acid, polyphosphoric acid, 4-toluenesulphonic acid, titanium iso-propoxide, aluminium trichloride, boron trifluoride diethyl etherate, or the like. Suitable reducing agents are hydrogen in the presence of a catalyst, preferably Pd, Pd—C, Pd(OH)$_2$, PtO$_2$, Rh—C or Raney-Nickel, sodium borohydride, sodium cyanoborohydride, lithium aluminumhydride, diborane, di-iso-butylaluminiumhydride, or the like. The reaction may be performed in the presence of one or more solvents which may be organic or inorganic, such as toluene, dichloromethane, ethers, alcohols, acetic acid, water, or in solvent mixtures.

$R^1$ and the substituents on W of compound (II), as defined above, may be modified after or during preparation of (I) from (I) and (M), by methods known in the art, for example reduction, oxidation and alkylation, after or during the preparation of (I) from (IV) and (V).

Compounds of formula (III), (IV) and (V) may be commercially available, prepared by literature procedures or prepared by methods known in the art.

The invention will now be described in more detail by way of the following examples, which should not in any way be regarded as limiting the invention.

EXAMPLES

Example 1

(i) Preparation of 4-[N-(1-benzyl-piperidin-4-yl)-amino]-N,N-diethyl Benzamide (Compound 1)

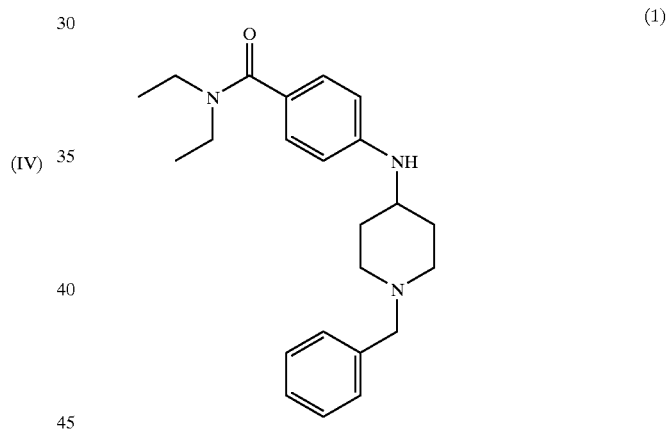

Ti(Oi—Pr)$_4$ (14.8 mL, 50 mmol) was added to a mixture of 4-amino-(N,N-diethyl)-benzamide (4.81 g, 25 mmol) and 1-benzyl-4-piperidone (6.95 mL, 37.5 mmol) at room temperature. The mixture was sonicated at 40° C. for 2 h, and stirred at 60° C. for 15 h. The mixture was cooled in an ice-bath and EtOH (100 mL) and NaBH$_4$ pellets (3.5 g, 91 mmol) were added. After stirring for 1 h at 0° C. and 20 h at room temperature, 1M NH$_4$OH (50 mL) was added. The mixture was stirred at room temperature for 30 min, diluted with CH$_2$Cl$_2$ (100 mL) and filtered through a pad of Celite®. The layers in the filtrate were separated, the aqueous layer extracted with CH$_2$Cl$_2$ (100 mL) and the combined organic phases washed with NaHCO$_3$ (aq., sat., 100 mL) and dried over K$_2$CO$_3$. The mixture was filtered, concentrated and the residue purified by chromatography (gradient, PhMe to Me$_2$CO) and crystallisation (PhMe) to give the title compound 1 (7.48 g, 82%) as a beige solid.

IR (KBr): 3343, 2939, 1608, 1528, 1459, 1422, 1339, 1285, 1174, 1091, 981, 827, 735 cm$^{-1}$.

$^1$H NMR (CDCl$_3$): 7.32 (d, 4H), 7.26 (t, 1H), 7.23 (d, 2H), 6.54 (d, 2H), 3.72 (broad s, 1H), 3.53 (s, 2H), 3.42 (broad d, 4H), 3.32 (broad s, 1H), 2.84 (d, 2H), 2.15 (t, 2H), 2.02 (d, 2H), 1.48 (q, 2H), 1.17 (t, 6H).

$^{13}$C NMR(CDCl$_3$): 171.7, 148.1, 138.3, 129.1, 128.5, 128.2, 127.0, 125.3, 112.2, 63.1, 52.2, 49.8, 41.5 (broad), 32.4, 13.6 (broad).

An analytical sample was prepared by recrystallisation from PhMe.

Anal. calcd. for C$_{23}$H$_{31}$N$_3$O: C, 75.58; H, 8.55; N, 11.50.
Found: C, 75.58; H, 8.63; N, 11.31.

(ii) Preparation f 4-[N-(1-benzyl-piperidin-4-yl)-anilin]-N,N-diethyl Benzamide (Compound 2)

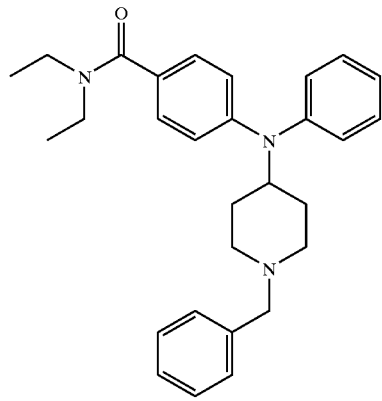

(2)

A mixture of 4-[N-(1-benzyl-piperidin-4-yl)-amino]-N,N-diethyl benzamide (compound 1) (0.58 g, 1.59 mmol), Ph$_3$Bi (0.84 g, 1.90 mmol) and Cu(OAc)$_2$ (0.43 g, 2.38 mmol) in PhMe (25 mL) was heated at 110° C. for 15 h. Ph$_3$Bi (0.84 g, 1.90 mmol) and Cu(OAc)$_2$ (0.43 g, 2.38 mmol) was added and the mixture was stirred at reflux for 6 h. Ph$_3$Bi (0.84 g, 1.90 mmol) and Cu(OAc)$_2$ (0.43 g, 2.38 mmol) was added, the mixture stirred at reflux for 15 h, allowed to cool and quenched with 1M NH$_4$OH (5 mL). The mixture was stirred at room temperature for 30 min, diluted with EtOAc (25 mL) and filtered through a pad of Celite®. The layers in the filtrate were separated, the deep blue aqueous layer extracted with EtOAc (25 mL) and the combined organic phases washed with H$_2$O (50 mL) and brine (25 mL) and dried over K$_2$CO$_3$. The mixture was filtered, concentrated and the residue purified by chromatography (gradient, PhMe to Me$_2$CO) to give the title compound 2 (0.33 g, 47%) as a colorless oil.

$^1$H NMR (CDCl$_3$): 7.53 (t, 2H), 7.29–7.18 (m, 8H), 7.01 (d, 2H), 6.58 (d, 2H), 3.85 (t, 1H), 3.49 (s, 2H), 3.42 (d, 4H), 2.95 (d, 2H), 2.11 (t, 2H), 1.92 (d, 2H), 1.51 (q, 2H), 1.17 (t, 6H).

$^{13}$C NMR (CDCl$_3$): 171.5, 149.0, 143.6, 138.2, 129.5, 129.1, 128.7, 128.2, 128.1, 127.0, 126.7, 125.4, 116.0, 63.1, 55.5, 53.3, 40 (broad), 30.7, 13 (broad).

An analytical sample was obtained as a hydrochloride by adding a solution of the free base in ether/EtOH to ice cold diluted etheral HCl.

IR (KBr): 3423, 2975, 2934, 2529, 1606, 1458, 1285, 1094, 750, 705 cm$^{-1}$.

Anal. calcd. for C$_{29}$H$_{35}$N$_3$O HCl*H$_2$O: C, 70.21; H, 7.72; N, 8.47
Found: C, 70.02; H, 7.61; N, 8.35

Example 2

Preparation of 4-[N-(1-benzyl-piperidin-4-yl)$_4$-methyl-anilino]-N,N-diethyl Benzamide (Compound 3)

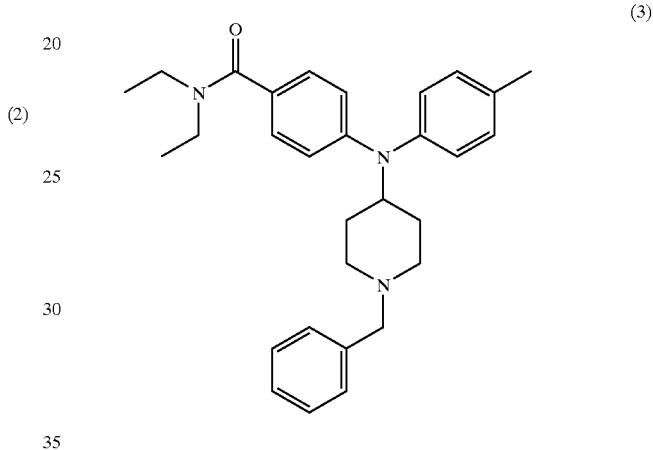

(3)

A mixture of 4-[N-(1-benzyl-piperidin-4-yl)-amino]-N,N-diethyl benzamide (compound 1) (0.37 g, 1.00 mmol), tri-4-tolylbismuth (1.59 g, 3.30 mmol) and Cu(OAc)$_2$ (0.54 g, 3.00 mmol) in PhMe (20 mL) was heated at reflux for 16 h. The mixture was allowed to cool and quenched with H$_2$O (2 mL). The mixture was stirred for 1 h, diluted with EtOAc (25 mL) and filtered through a pad of Celite®. The layers in the filtrate were separated, the aqueous layer extracted with EtOAc (25 mL) and the combined organic phases washed with H$_2$O (50 mL) and brine (25 mL) and dried over MgSO$_4$. The mixture was filtered, concentrated and the residue purified by chromatography (gradient, CH$_2$Cl$_2$ to 8% MeOH/CH$_2$Cl$_2$) to give the title compound 3 (0.09 g, 20%) as a colorless oil.

$^1$H NMR (CDCl$_3$): 7.30–7.16 (m, 9H), 6.94 (d, 2H), 6.52 (d, 2H), 3.83 (t, 1H), 3.48 (s, 2H), 3.42 (d, 4H), 2.93 (d, 2H), 2.36 (s, 3H), 2.07 (t, 2H), 1.90 (d, 2H), 1.50 (q, 2H), 1.16 (t, 6H).

$^{13}$C NMR(CDCl$_3$): 171.6, 149.7, 140.4, 138.2, 136.1, 130.2, 130.2, 129.0, 128.1, 128.0, 126.9, 125.3, 113.8, 63.0, 55.4, 53.3, 41 (broad), 30.5, 21.0, 13 (broad).

An analytical sample was obtained as a hydrochloride by adding an etheral solution of the free base to ice cold diluted etheral HCl.

IR (KBr): 2936, 2528, 1605, 1510, 1457, 1428, 1284, 1094, 952, 742, 701 cm$^{-1}$.

Anal. calcd. for C$_{30}$H$_{37}$N$_3$O HCl*0.5 H$_2$O: C, 71.91; H, 7.84; N, 8.39
Found: C, 71.75; H, 7.83; N, 8.32

Example 3

Preparation of 4-[N-(1-benzyl-piperidin-4-yl)-1-naphtylamin]-N,N-diethyl Benzamide (Compound 4)

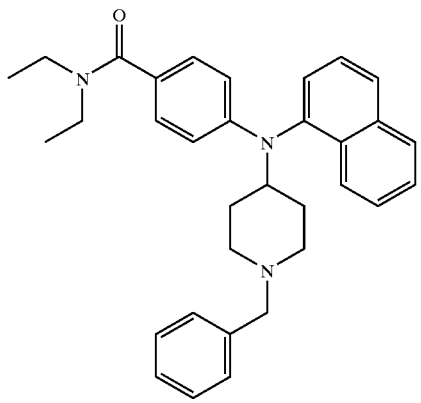

(4)

A mixture of 4-[N-(1-benzyl-piperidin-4-yl)-amino]-N,N-diethyl benzamide (compound 1) (0.37 g, 1.00 mmol), tri-1-naphtylbismuth (0.53 g, 1.20 mmol) and Cu(OAc)$_2$ (0.27 g, 1.50 mmol) in PhMe (20 mL) was heated at reflux for 17 h. Tri-1-naphtylbismuth (0.53 g, 1.20 mmol) and Cu(OAc)$_2$ (0.27 g, 1.50 mmol) was added at room temperature. The mixture was stirred at reflux for 22 h, allowed to cool and quenched with 1M NH$_4$OH (5 mL). The mixture was stirred for 30 min, diluted with EtOAc (25 mL) and filtered through a pad of Celite®. The layers in the filtrate were separated, the deep blue aqueous layer extracted with EtOAc (25 mL) and the combined organic phases washed with H$_2$O (50 mL) and brine (25 mL) and dried over K$_2$CO$_3$. The mixture was filtered, concentrated and the residue purified by chromatography (gradient, PhMe to Me$_2$CO) to give the title compound 4 (0.41 g, 83%) as a brownish solid.

IR(KBr): 2939, 2796, 1619, 1511, 1456, 1420, 1346, 1282, 1180, 1099, 783 cm$^{-1}$.

$^1$H NMR (CDCl$_3$): 7.87 (t, 2H), 7.79 (d, 1H), 7.51 (t, 1H), 7.46 (t, 1H), 7.37 (t, 1H), 7.31 (d, 1H), 7.28–7.19 (m, 5H), 7.17 (d, 2H), 6.41 (d, 2H), 4.08 (t, 1H), 3.46 (s, 2H), 3.40 (d, 4H), 2.89 (d, 2H), 2.11 (t, 2H), 2.08 (broad s, 2H), 1.50 (broad s, 2H), 1.14 (t, 6H).

$^{13}$C NMR (CDCl$_3$): 171.7, 149.8, 138.9, 138.1, 135.0, 133.4, 129.1, 129.0, 128.3, 128.2, 128.1, 128.0, 127.0, 126.4, 126.2, 126.1, 124.6, 124.5, 112.2, 63.0, 56.5, 53.3, 40 (broad), 30.4, 13.5 (broad).

An analytical sample was obtained by recrystallization from EtOH

Anal. calcd. for C$_{33}$H$_{37}$N$_3$O: C, 80.61; H, 7.59; N, 8.55

Found: C, 80.48; H, 7.41; N, 8.52

Example 4

Preparation of 4-[N-(1-benzyl-piperidin-4-yl)-2-naphtylamino]-N,N-diethyl Benzamide (Compound 5)

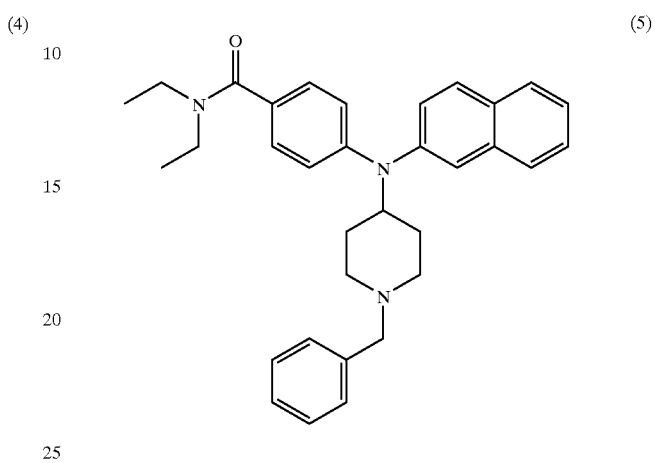

(5)

A mixture of 4-[N-(1-benzyl-piperidin-4-yl)-amino]-N,N-diethyl benzamide (compound 1) (0.67 g, 1.83 mmol), tri-2-naphtylbismuth (0.97 g, 2.20 mmol) and Cu(OAc)$_2$ (0.50 g, 2.75 mmol) in PhMe (35 mL) was heated at reflux for 15 h. Tri-2-naphtylbismuth (0.97 g, 2.20 mmol) and Cu(OAc)$_2$ (0.50 g, 2.75 mmol) was added, and the mixture was stirred at reflux for 22 h. Tri-2-naphtylbismuth (0.97 g, 2.20 mmol) and Cu(OAc)$_2$ (0.50 g, 2.75 mmol) was added. After reflux for 70 h the mixture was allowed to cool and quenched with 1M NH$_4$OH (10 mL). The mixture was stirred for 30 min, diluted with EtOAc (35 mL) and filtered through a pad of Celite®. The layers in the filtrate were separated, the deep blue aqueous layer extracted with EtOAc (35 mL) and the combined organic phases washed with H$_2$O (75 mL) and brine (35 mL) and dried over MgSO$_4$. The mixture was filtered, concentrated and the residue purified by chromatography (gradient, PhMe to Me$_2$CO) to give the title compound 5 (0.63 g, 70%) as a brown oil that solidified on standing.

IR (KBr): 2935, 2807, 1614, 1510, 1424, 1284 cm$^{-1}$.

$^1$H NMR (CDCl$_3$): 7.83–7.78 (m, 2H), 7.74 (d, 1H), 7.48–7.42 (m, 3H), 7.27–7.21 (m, 7H), 7.10 (dd, 1H), 6.66 (d, 2H), 3.94 (t, 1H), 3.48 (s, 2H), 3.43 (broad s, 4H), 2.94 (d, 2H), 2.14 (t, 2H), 1.99 (s, 2H), 1.57 (m, 2H), 1.17 (t, 6H).

$^{13}$C NMR(CDCl$_3$): 171.4, 148.8, 141.3, 138.1, 134.2, 131.2, 129.2, 129.0, 128.1, 128.0, 127.5, 127.4, 127.2, 126.9, 126.2, 125.4, 125.3, 116.8, 63.0, 55.8, 53.3, 41 (broad), 30.7, 13.6 (broad).

An analytical sample was obtained from MeOH.

Anal. calcd. for C$_{33}$H$_{37}$N$_3$O: C, 80.61; H, 7.59; N. 8.55

Found: C, 80.35; H, 7.59; N, 8.46

Example 5

Preparation of N,N-diethyl-4-(N-piperidin-4-yl-anilino) Benzamide (Compound 6)

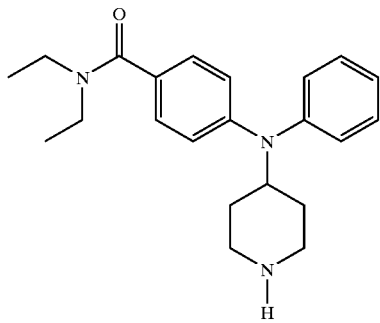

(6)

A solution of 4-[N-(1-benzyl-piperidin-4-yl)-anilino]-N,N-diethyl benzamide (compound 2) (1.21 g, 2.74 mmol) in MeOH (25 mL) was hydrogenated at 60 psi for 4 d in the presence of a catalytic amount of Pd(OH)$_2$ on carbon. The mixture was filtered through a pad of Celite, concentrated and the residue purified by chromatography (gradient, CH$_2$Cl$_2$ to CH$_2$Cl$_2$/MeOH (9:1) to CH$_2$Cl$_2$/MeOH/NH$_4$OH (aq., conc.) (80:18:2) to give the title compound 6 (0.62 g, 64%) as a colorless oil.

$^1$H NMR (CDCl$_3$): 7.37 (t, 2H), 7.25–7.22 (m, 3H), 7.01 (d, 2H), 6.61 (d, 2H), 3.98 (t, 1H), 3.42 (broad d, 4H), 3.17 (d, 2H), 2.78 (t, 2H), 2.00 (d, 2H), 1.71 (broad s, 1H), 1.41 (q, 2H), 1.18 (t, 6H).

$^{13}$C NMR (CDCl$_3$): 171.4, 148.2, 143.1, 129.8, 128.0, 127.9, 127.7, 125.7, 116.9, 53.5, 44.4, 41 (broad), 28.7, 13.5 (broad).

An analytical sample was obtained as a hydrochloride by adding an etheral solution of the free base to ice cold diluted etheral HCl.

IR (KBr): 3426, 3359, 2936, 2722, 1603, 1473, 1281, 1091, 708, 503 cm$^{-1}$.

Anal. calcd. for C$_{22}$H$_{29}$N$_3$O HCl*H$_2$O: C, 65.09; H, 7.95; N, 10.35

Found: C, 65.37; H, 7.94; N, 10.38

Example 6

Preparation of N,N-diethyl-4-([N-piperidin-4-yl]-1-naphtylamino Benzamide (Compound 7)

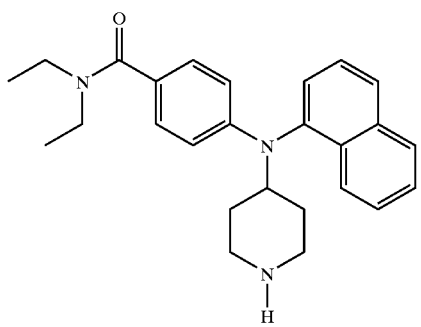

(7)

A solution of 4-[N-(1-benzyl-piperidin-4-yl)-1-naphtylamino]-N,N-diethyl benzamide (compound 4) (0.22 g, 0.45 mmol) in EtOH (20 mL) was hydrogenated at 60 psi for 64 h in the presence of a catalytic amount of Pd(OH)$_2$ on carbon. The mixture was filtered through a pad of Celite®, concentrated and the residue purified by chromatography (gradient, CH$_2$Cl$_2$ to CH$_2$Cl$_2$/MeOH (9:1) to CH$_2$Cl$_2$/MeOH/NH$_4$OH (aq., conc.) (80:18:2)) to give the title compound 7 (0.12 g, 67%) as a colorless oil that solidified on standing.

IR (KBr): 2942, 1609, 1512, 1448, 1280 cm$^{-1}$.

$^1$H NMR (CDCl$_3$): 7.86 (t, 2H), 7.80 (d, 1H), 7.50 (t, 1H), 7.45 (t, 1H), 7.36 (t, 1H), 7.30 (d, 1H), 7.18 (d, 2H), 6.42 (d, 2H), 4.20 (t, 1H), 3.40 (broad d, 4H), 3.06 (d, 2H), 2.79–2.63 (m, 3H), 2.03 (broad s, 2H), 1.39 (broad s, 2H), 1.14 (t, 6H).

$^{13}$C NMR (CDCl$_3$): 171.6, 149.4, 138.7, 134.8, 133.3, 128.7, 128.2, 128.1, 127.9, 126.3, 126.1, 126.0, 124.4, 124.2, 112.1, 56.1, 46.0, 41 (broad), 31.3, 13.4 (broad).

Anal. calcd. for C$_{26}$H$_{31}$N$_3$O*1.25H$_2$O: C, 73.64; H, 7.96; N, 9.91

Found: C, 73.77; H, 7.54; N, 9.96

Example 7

Preparation of N,N-diethyl-4-([N-piperidin-4-yl]-2-naphtylamino Benzamide (Compound 8)

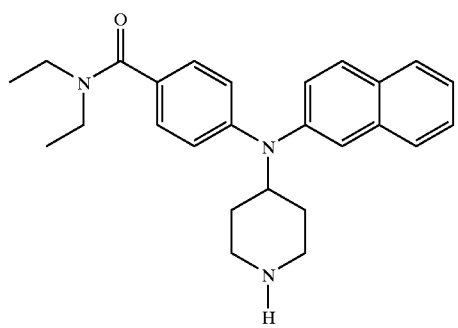

(8)

(1-chloroethyl) chloroformate (58 μL, 0.53 mmol) was added to a solution of 4-[N-(1-benzyl-piperidin-4-yl)-2-naphtylamino]-N,N-diethyl benzamide (compound 5) (105 mg, 0.21 mmol) in dichloroethane (2.5 mL) at room temperature. The mixture was heated at reflux for 17 h and was then allowed to cool to room temperature and concentrated. Methanol (2.5 mL) was added and the mixture was heated at reflux for 2.5 h, allowed to cool and concentrated. The residue was partitioned between CH$_2$Cl$_2$ (10 mL) and 1M NH$_4$OH (10 mL). The layers were separated and the organic phase was washed with H$_2$O (10 mL) and brine (10 mL) and dried over K$_2$CO$_3$. The mixture was filtered, concentrated and the the residue purified by chromatography (gradient, CH$_2$Cl$_2$ to CH$_2$Cl$_2$/MeOH/NH$_4$OH (aq., conc.) (85:13.5:1.5) and HPLC (LiChroPrep RP-18, eluation with increasing amounts of 0.1% TFA/MeCN in 0.1% TFA/H$_2$O) to give the title compound 8 (30 mg) as the trifluoroacetate.

IR (neat): 3420, 1680, 1600 cm$^{-1}$.

$^1$H NMR (CDCl$_3$, TFA salt) d: 1.10 (6H, m), 1.78 (2H, m,), 2.10 (2H, m, CH(CH)CH(N)CH(CH)), 3.00 (2H, m, CH(CH)NHCH(CH)), 3.35 (6H, m), 4.15 (1H, m,), 6.65 (2H, m), 7.00 (1H, m), 7.20 (2H, m), 7.40 (3H, m), 7.75 (3H, m, Ar).

Example 8

Preparation of 4-[N-(1-[2-phenylethyl]-piperidin-4-yl)-anilino]-N,N-diethyl-benzamide (Compound 9)

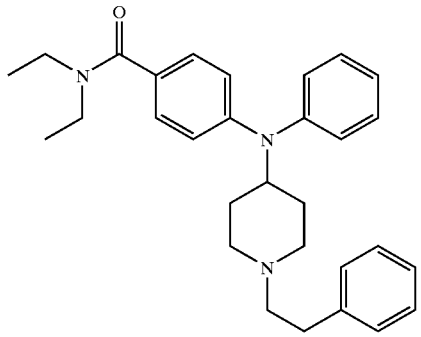

(9)

(2-bromoethyl)benzene (0.18 mL, 1.30 mmol) was added with stirring to an ice-cold solution of N,N-diethyl-4-(N-piperidin-4-yl-anilino) benzamide (compound 6) (0.21 g, 0.59 mmol), Et$_3$N (0.10 ml, 0.75 mmol) and a catalytic amount of 4-dimethyl aminopyridine in CH$_2$Cl$_2$ (5 mL). The stirred mixture was allowed to attain room temperature over 5 h, heated at reflux for 16 h, allowed to cool to room temperature, diluted with CH$_2$Cl$_2$ (10 mL) and washed with H$_2$O (15 mL), brine (15 mL) and dried over K$_2$CO$_3$. The mixture was filtered, concentrated and the residue purified by chromatography (gradient, PhMe to PhMe/Me$_2$CO (1:2)) to give the title compound 9 (0.11 g, 40%) as a colorless oil which solidified on standing.

IR (KBr): 2928, 1612, 1504, 1437, 1280, 1980, 754 cm$^{-1}$.

$^1$H NMR (CDCl$_3$): 7.36 (t, 2H), 7.30–7.15 (m, 8H), 7.01 (d, 2H), 6.61 (d, 2H), 3.88 (t, 1H), 3.42 (broad d, 4H), 3.08 (d, 2H), 2.76 (m, 2H), 2.57 (m, 2H), 2.17 (t, 2H), 1.97 (d, 2H), 1.55 (q, 2H), 1.18 (t, 6H).

$^{13}$C NMR (CDCl$_2$): 171.5, 149.0, 143.5, 140.3, 129.6, 128.6, 128.6, 128.4, 128.1, 126.8, 126.1, 125.4, 116.1, 60.6, 55.5, 53.5, 41 (broad), 33.9, 30.7, 13.6 (broad).

Anal. calcd. for C$_{30}$H$_{37}$N$_3$O*0.2 C$_3$H$_6$O: C, 78.66; H, 8.24; N, 8.99.

Found: C, 78.55; H, 7.75; N, 8.91.

Example 9

(i) Preparation of 3-[N-(1-benzyl-piperidin-4-yl)-amino]-N,N-diethyl Benzamide (Compound 10)

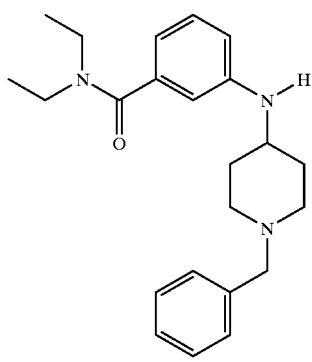

(10)

Ti(Oi—Pr)$_4$ (0.70 ml, 2.37 mmol) was added to a mixture of 3-amino-(N,N-diethyl) benzamide (150 mg, 0.78 mmol) and 1-benzyl-4-piperidone (0.18 mL, 0.97 mmol) at room temperature. The mixture was sonicated at 40° C. for 6 h, and stirred at room temperature for 15 h. The mixture was cooled in an ice-bath and EtOH (5 mL) and NaBH$_4$ (75 mg, 1.98 mmol) were added. After stirring for 1 h at 0° C. and 2 d at room temperature, 2M NH$_4$OH (5 mL) was added. The mixture was stirred at room temperature for 30 min, diluted with CH$_2$Cl$_2$ (10 mL) and filtered through Celite®. The layers in the filtrate were separated, the aqueous layer extracted with CH$_2$Cl$_2$ (3×10 mL). The combined organic phases were washed with 10% HCl (2×15 mL). The pH in the combined aqueous extracts was adjusted to 10 with 2N NaOH, and extracted with CH$_2$Cl$_2$ (3×10 mL). The combined organic extracts were dried over Na$_2$SO$_4$, filtered, concentrated and the residue purified by chromatography (9:1:0.1 EtOAc:heptane: Et$_3$N) to give the title compound 10 (173 mg, 61%) as a pale yellow thick oil.

IR (neat): 3333,1612 cm$^{-1}$.

$^1$H NMR (CDCl$_3$): 7.40–7.10 (7H, m), 6.55 (2H, m), 3.50 (4H, m), 3.22 (4H, m), 2.80 (2H, m), 2.12 (2H, m), 2.00 (2H, m), 1.43 (2H, m), 1.20 (3H, m), 1.05 (3H, m).

$^{13}$C NMR(CDCl$_3$): 171.6, 147.1, 138.3, 138.2, 129.1, 129.0, 128.1, 126.9, 114.6, 113.8, 110.6, 63.0, 52.2, 49.8, 43.1, 38.9, 32.4, 14.1, 12.8.

Anal. calcd. for C$_{23}$H$_{31}$N$_3$O HCl*2.1H$_2$O: C, 63.07; H, 8.28; N, 9.59.

Found: C, 63.19; H, 7.94; N, 9.25.

(ii) Preparation of 3-[N-(1-benzyl-piperidin-4-yl)-anilino]-N,N-diethyl Benzamide (Compound 11)

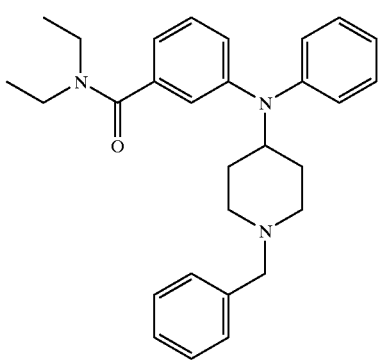

(11)

A mixture of 3-[N-(1-benzyl-piperidin-4-yl)-amino]-N, N-diethyl benzamide (compound 10) (360 mg, 0.98 mmol), Ph$_3$Bi (1.10 g, 2.50 mmol), and Cu(OAc)$_2$ (0.45 g, 2.48 mmol) in toluene (10 mL) was heated at 110° C. for 12 h. Another portion of Cu(OAc)$_2$ (0.45 g) was added and the mixture was heated at 110° C. for an additional 12 h and allowed to cool to room temperature. Water (10 mL) was added and the mixture filtered through Celite®. The layers in the filtrate were separated, and the organic phase was washed with water, brine, dried over Na$_2$SO$_4$ and concentrated. Chromatography of the residue (9:1 EtOAc/heptane) gave the title compound 11 (255 mg, 59%) as a pale yellow thick oil.

IR (neat): 3056, 3010, 2937, 2810, 1629 cm$^{-1}$.

$^1$H NMR (CDCl$_3$): 7.40–6.60 (14H, m), 3.80 (1H, m), 3.43 (4H, bs), 3.20 (2H, bs), 2.90 (2H, m), 2.05 (2H, m), 1.90 (2H, m), 1.48 (2H, m), 1.20 (3H, bs), 1.00 (3H, bs).

$^{13}$C NMR (CDCl$_3$): 171.3, 147.3, 144.4, 138.1, 129.3, 129.0, 128.0, 126.9, 126.4, 123.9, 119.7, 117.5, 116.5, 62.9, 55.3, 53.2, 43.0, 39.0, 30.6, 14.0, 12.7.

Anal. calcd. for C$_{29}$H$_{35}$N$_3$O 1.25 HCl*0.5 H$_2$O: C, 70.15; H, 7.41; N, 8.47; Cl, 8.94.

Found: C, 69.69; H, 7.34; N, 8.25; Cl, 8.96.

Example 10

Preparation of N,N-diethyl-3-(N-piperidin-4-yl-anilino) Benzamide (Compound 12)

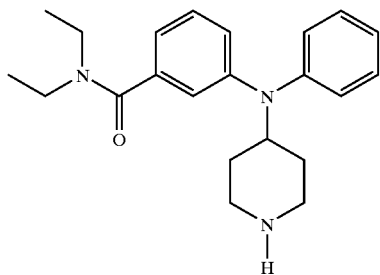

(12)

A solution of 3-[N-(1-benzyl-piperidin-4-yl)-anilino]-N,N-diethyl benzamide (compound 11) (102 mg, 0.23 mmol) in EtOH (15 mL) was hydrogenated at 40 psi in the presence of a catalytic amount of Pd(OH)$_2$ on carbon for 2 h. The mixture was filtered through Celite® and concentrated. The residue was purified by chromatography (9:1:0.5 EtOAc/heptane/Et$_3$N) to yield the title compound 12 (50 mg, 81%) as a pale yellow viscous oil.

IR: (HCl-salt, neat) 3421, 1597, 1494 cm$^{-1}$.

$^1$H NMR (CDCl$_3$): 7.80–6.50 (9H, m), 4.00 (1H, m), 3.21 (2H, bs), 3.30 (2H, m), 3.20 (2H, bs), 2.90 (2H, m), 2.05 (2H, m), 1.70 (2H, m), 1.17 (3H, bs), 1.00 (3H, bs).

$^{13}$C NMR(CDCl$_3$): 171.0, 143.7, 140.7, 138.0, 129.5, 129.2, 128.2, 124.5, 119.7, 117.9, 116.5, 53.2, 43.1, 41.1, 39.0, 28.7, 14.0, 8.9.

An analytical sample was obtained as a hydrochloride by adding an etheral solution of the free base to ice cold diluted etheral HCl.

Anal. calcd. for C$_{28}$H$_{33}$N$_3$O*HCl*1.3H$_2$O: C, 62.30; H, 8.08; N, 9.91.

Found: C, 62.40; H, 7.67; N, 9.80.

Example 11

(i) Preparation of 4-[N-(1-benzyl-piperidin-3-yl)-amino]-N,N-diethyl Benzamide (Compound 13)

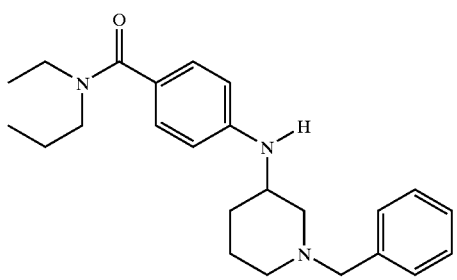

(13)

Ti(Oi—Pr)$_4$ (2.2 mL, 7.45 mmol) was added to a mixture of 4-amino-(N,N-diethyl) benzamide (0.36 g, 1.87 mmol) and 1-benzyl-3-piperidone (0.70 g, 3.69 mmol) at room temperature. The mixture was sonicated at 40° C. for 1 h, and stirred at room temperature for 15 h. The mixture was cooled in an ice-bath and EtOH (15 mL) and NaBH$_4$ (0.21 g, 5.55 mmol) were added. After stirring for 16 h at room temperature, 2M NH$_4$OH (15 mL) was added. The mixture was stirred at room temperature for 30 min, diluted with CH$_2$Cl$_2$ (10 mL) and filtered through a pad of Celite®. The layers in the filtrate were separated, the aqueous layer extracted with CH$_2$Cl$_2$ (3×15 mL). The combined organic phases were washed with 10% HCl (2×20 mL). The pH in the combined aqueous extracts was adjusted to 10 with 2N NaOH, and extracted with CH$_2$Cl$_2$ (3×10 mL). The combined organic extracts were dried over Na$_2$SO$_4$, filtered and concentrated. The residue was purified by chromatography (9:1:0.1 EtOAc/heptane/Et$_3$N) to give the title compound 13 (0.32 g, 47%) as a pale yellow thick oil.

IR (neat): 3320, 1736, 1608 cm$^{-1}$.

$^1$H NMR (CDCl$_3$): 7.20 (7H, m), 6.50 (2H, m), 4.22 (1H, bs), 3.60–3.30 (7H, m), 2.60 (1H, m), 2.35 (3H, m), 1.65 (2H, m), 1.50 (2H, m), 1.10 (6H, m).

$^{13}$C NMR(CDCl$_3$): 171.7, 147.9, 138.1, 128.7, 128.4, 128.1, 126.9, 124.9, 112.1, 63.0, 58.6, 53.5, 48.3, 41.4, 28.6, 22.3, 13.4.

Anal. calcd. for C$_{23}$H$_{31}$N$_3$O*HCl*2.1H$_2$O: C, 62.81; H, 8.30; N, 9.55.

Found: C, 62.75; H, 7.94; N, 9.63.

(ii) Preparation of 4-[N-(1-benzyl-piperidin-3-yl)-anilino]-N,N-diethyl Benzamide (Compound 14)

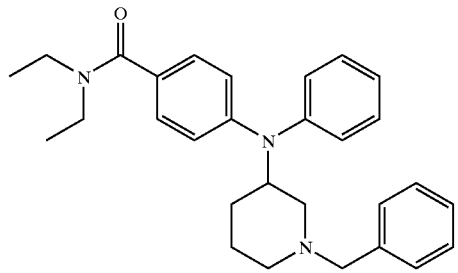

(14)

A mixture of 4-[N-(1-benzyl-piperidin-3-yl)-amino]-N,N-diethyl benzamide (compound 13) (0.29 mg, 0.79 mmol), Ph$_3$Bi (0.87 g, 1.98 mmol), and Cu(OAc)$_2$ (0.36 g, 1.98 mmol) in toluene (5 mL) was heated at 110° C. for 12 h and allowed to cool to room temperature. Water (5 mL) was added and the mixture filtered through Celite®. The layers in the filtrate were separated and the organic phase washed with water, brine, dried over Na$_2$SO$_4$ and concentrated. Chromatography of the residue (9:1 EtOAc/heptane) gave the title compound 14 (0.24 g, 67%) as a pale yellow viscous oil.

IR (neat): 3056, 3012, 2938, 2800, 1613, 1492 cm$^{-1}$.

$^1$H NMR (CDCl$_3$): 7.40–7.10 (10H, m), 6.95 (2H, d), 6.55 (2H, d), 4.05 (1H, m), 3.45 (2H, s), 3.38 (4H, bs), 3.19 (1H), 2.75 (1H, m), 1.90 (1H, m), 1.80–1.60 (4H, m), 1.12 (6H, m).

An analytical sample was obtained as a hydrochloride by adding an etheral solution of the free base to ice cold diluted etheral HCl.

$^{13}$C NMR (CDCl$_3$): 171.4, 148.8, 143.4, 138.2, 129.3, 128.7, 128.6, 128.4, 128.0, 127.8, 126.8, 125.3, 123.9, 115.7, 62.9, 57.2, 54.4, 53.2, 42(b), 29.8, 25.9, 13.4(b).

Anal. calcd. for C$_{29}$H$_{35}$N$_3$O*1.25 HCl*0.5H$_2$O: C, 70.15; H, 7.41; N, 8.47; Cl, 8.94.

Found: C, 70.30; H, 7.30; N, 8.43; Cl, 8.34.

Example 12

Preparation of N,N-Diethyl-4-(N-piperidin-3-yl-anilino) Benzamide (Compound 15)

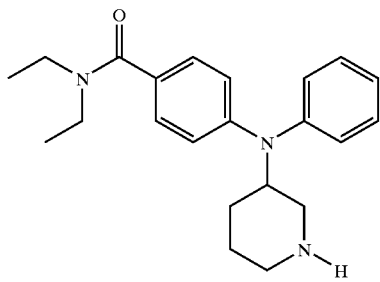
(15)

A solution of 4-[N-(1-benzyl-piperidin-3-yl)-anilino]-N,N-diethyl benzamide (compound 14) (0.28 g, 0.63 mmol) in EtOH (10 mL) was hydrogenated at 30 psi in the presence of a catalytic amount of Pd(OH)$_2$ on carbon for 6 h. The mixture was filtered through Celite®, concentrated and the residue purified by chromatography (gradient, 9:1:0 to 9:1:0.5 EtOAc/heptane/Et$_3$N) to yield the title compound 15 (80 mg, 36%) as a pale yellow viscous oil.

IR:(neat) 3300–3500, 1609, 1464 cm$^{-1}$.

$^1$H NMR (CDCl$_3$): 7.35 (2H, m), 7.18 (3H, m), 6.95 (2H, m), 6.56 (2H, m), 4.30 (1H, bs), 4.0 (1H, m), 3.38 (4H, bs), 2.95 (1H, m), 2.35 (2H, m), 1.95 (1H, m), 1.70 (2H, m), 1.15 (2H, m), 1.10 (6H, m).

$^{13}$C NMR (CDCl$_3$): 171.3, 148.5, 142.8, 129.3, 128.5, 127.7, 126.4, 125.5, 115.4, 54.1, 49.3, 45.4, 44–38(b), 29.9, 25.6, 13.3(b).

Anal. calcd. for C$_{22}$H$_{29}$N$_3$O*HCl*0.4H$_2$O: C, 66.87; H, 7.86; N, 10.63.

Found: C, 66.85; H, 7.68; N, 10.44.

Example 13

(i) Preparation of 3-[N-(1-benzyl-piperidin-3-yl)-amino]-N,N-diethyl Benzamide (Compound 16)

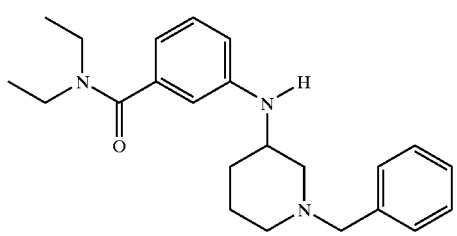
(16)

Ti(Oi—Pr)$_4$ (6.2 mL, 21.0 mmol) was added to a mixture of 3-amino-(N,N-diethyl) benzamide (1.0 g, 5.2 mmol) and 1-benzyl-3-piperidone (2.0 g, 10.6 mmol) at room temperature. The mixture was sonicated at 40° C. for 2 h, and stirred at room temperature for 16 h. The mixture was cooled in an ice-bath and EtOH (30 mL) and NaBH$_4$ (0.60 g, 15.9 mmol) were added. After stirring for 16 h at room temperature, 2M NH$_4$OH (25 mL) was added. The mixture was stirred at room temperature for 30 min, diluted with CH$_2$Cl$_2$ (25 mL) and filtered through a pad of Celite®. The layers in the filtrate were separated and the aqueous layer extracted with CH$_2$Cl$_2$ (3×25 mL). The combined organic phases were washed with 10% HCl (2×25 mL). The pH in the combined aqueous extracts was adjusted to 10 with 2N NaOH, and extracted with CH$_2$Cl$_2$ (3×25 mL). The combined organic extracts were dried over Na$_2$SO$_4$, filtered and concentrated. The residue was purified by chromatography (9:1:0.1 EtOAc/heptane/Et$_3$N) to give the title compound 16 (1.10 g, 58%) as a pale yellow viscous oil.

IR(neat): 3327,1606 1440 cm$^{-1}$.

$^1$H NMR (CDCl$_3$): 7.40–7.00 (7H, m), 6.60–6.40 (2H, m), 4.20 (1H, bs), 3.50 (4H, m), 3.20 (2H, bs), 2.60 (1H, m), 2.40–2.20 (3H, m), 1.70 (2H, m), 1.50 (2H, m), 1.20 (3H, bs), 1.00 (3H, bs).

$^{13}$C NMR(CDCl$_3$): 171.4, 146.9, 138.1, 137.9, 128.9, 128.6, 127.9, 126.7, 114.1, 113.5, 110.4, 62.8, 58.5, 53.3, 48.3, 42.9, 38.7, 28.6, 22.2, 13.9, 12.6.

(ii) Preparation of 3-[N-(1-benzyl-piperidin-3-yl)-anilino]-N,N-diethyl Benzamide (Compound 17)

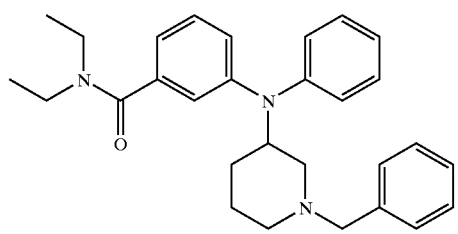
(17)

A mixture of 3-[N-(1-Benzyl-piperidin-3-yl)-amino]-N,N-diethyl benzamide (compound 16) (0.25 g, 0.68 mmol), Ph$_3$Bi (0.75 g, 1.70 mmol), and Cu(OAc)$_2$ (0.31 mg, 1.70 mmol) in toluene (5 mL) was heated at 110° C. for 14 h and allowed to cool to room temperature. Water (5 mL) was added and the mixture was filtered through Celite®. The layers in the filtrate were separated and the organic phase was washed with water and brine, dried over Na$_2$SO$_4$ and concentrated. Chromatography of the residue (9:1 EtOAc/heptane) gave the title compound 17 (0.16 g, 52%) as a pale yellow viscous oil.

IR (neat): 3010, 2930, 1630, 1610 cm$^{-1}$.

$^1$H NMR (CDCl$_3$): 7.40–6.60 (14H, m), 4.05 (1H, m), 3.45 (4H, bs), 3.18 (2H, m), 2.75 (1H, m), 1.90 (1H, m), 1.80–1.60 (4H, m), 1.18 (3H, bs), 1.00 (3H, bs).

$^{13}$C NMR (CDCl$_3$): 171.3, 147.1, 144.5, 138.3, 138.1, 129.3, 129.1, 128.8, 128.1, 126.9, 125.9, 123.7, 119.8, 117.8, 116.9, 63.0, 57.5, 54.4, 53.2, 43.1, 39.0, 29.9, 25.0, 14.1, 12.8.

Anal. calcd. for C$_{29}$H$_{35}$N$_3$O*1.4HCl*0.5H$_2$O: C, 69.38; H, 7.46; N, 8.37; Cl, 9.91.

Found: C, 69.11; H, 7.14; N, 8.08; Cl, 10.12.

Example 14

Preparation of N,N-Diethyl-3-(N-piperidin-3-yl-anilino) Benzamide (Compound 18)

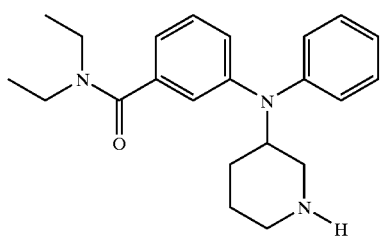
(18)

A solution of 3-[N-(1-benzyl-piperidin-3-yl)-anilino]-N,N-diethyl benzamide (compound 17) (50 mg, 0.11 mmol) in EtOH (5 mL) was hydrogenated at 30 psi in the presence of a catalytic amount of Pd(OH)$_2$ on carbon for 6 h. The mixture was filtered through Celite®, concentrated and the residue purified by chromatography (gradient, 9:1:0 to 9:1:0.5 EtOAc/heptane/Et$_3$N) to yield the title compound 18 (15 mg, 36%) as a pale yellow viscous oil.

$^1$H NMR (CDCl$_3$): 7.40–6.60 (9H, m), 4.40 (1H, m), 3.60 (2H, m),), 3.40 (2H, bs), 3.15 (3H, m), 2.50 (2H, m), 1.80 (2H), 1.20 (2H, m), 1.18 (3H, bs), 0.95 (3H, bs).

$^{13}$C NMR(CDCl$_3$): 171.2, 146.9, 144.0, 138.0, 129.4, 126.4, 124.3, 119.7, 117.8, 116.5, 54.1, 45.1, 43.1, 39.0, 30.0, 14.0, 12.7.

An analytical sample was obtained as a hydrochloride by adding an etheral solution of the free base to ice cold diluted etheral HCl.

IR: (neat) 3412,1598,1493 cm$^{-1}$.

Anal. calcd. for C$_{22}$H$_{29}$N$_3$O*HCl*H$_2$O: C, 65.09; H, 7.95; N, 10.35.

Found: C, 65.03; H, 7.80; N, 10.02.

Example 15

(i) Preparation of 4-[N-(1-benzyl-pyrrolidin-3-yl)-amino]-N,N-diethyl Benzamide (Compound 19)

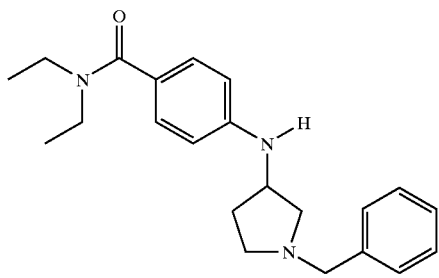
(19)

Ti(Oi—Pr)$_4$ (3.1 ml, 10.4 mmol) was added to a mixture of 4-amino-(N,N-diethyl) benzamide (0.50 g. 2.51 mmol) and 1-benzyl-3-pyrrolidone (0.85 mL, 5.30 mmol) at room temperature. The mixture was sonicated at 40° C. for 3 h, and stirred at room temperature for 16 h. The mixture was cooled in an ice-bath and EtOH (30 mL) and NaBH$_4$ (0.30 g, 8.00 mmol) were added. After stirring for 16 h at room temperature, 2M NH$_4$OH (20 mL) was added. The mixture was stirred at room temperature for 30 min, diluted with CH$_2$Cl$_2$ (20 mL) and filtered through a pad of Celite®. The layers in the filtrate were separated, the aqueous layer extracted with CH$_2$Cl$_2$ (3×20 mL). The combined organic phases were washed with 10% HCl (2×20 mL). The pH in the combined aqueous extracts was adjusted to 10 with 2N NaOH, and extracted with CH$_2$Cl$_2$ (3×20 mL). The combined organic extracts were dried over Na$_2$SO$_4$, filtered, concentrated and the residue purified by chromatography (gradient, 9:1:0.5 to 9:0:1 EtOAc/heptane/Et$_3$N) to give the title compound 19 (0.40 g, 44%) as a pale yellow viscous oil.

IR (neat): 3322,1609,1527,1455 cm$^{-1}$.

$^1$H NMR (CDCl$_3$): 7.40–7.10 (7H, m), 6.60–6.40 (2H, m), 4.20 (1H, m), 3.95 (1H, m), 3.55 (2H, s), 3.35 (4H, bs), 2.70 (2H, m), 2.50–2.35 (2H, m), 2.25 (1H, m), 1.60 (1H, m), 1.15 (6H, bt).

$^{13}$C NMR(CDCl$_3$): 171.4, 148.2, 138.4, 128.5, 128.2, 128.1, 126.7, 126.1, 113.8, 112.1, 60.5, 59.9, 52.5, 51.9, 41 (b), 32.2, 13.3.

(ii) Preparation of 4-[N-(1-benzyl-pyrrolidin-3-yl)-anilino]-N,N-diethyl Benzamide (Compound 20)

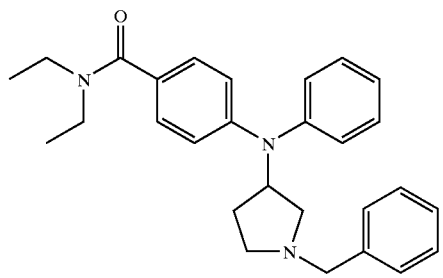
(20)

A mixture of 4-[N-(1-benzyl-pyrrolidin-3-yl)-amino]-N,N-diethyl benzamide (compound 19) (0.40 g, 1.14 mmol), Ph$_3$Bi (1.25 g, 2.84 mmol), and Cu(OAc)$_2$ (0.52 g, 2.86 mmol) in toluene (10 mL) was heated at 110° C. for 16 h and allowed to cool to room temperature. Water (5 mL) was added and the mixture was filtered through Celite®. The filtrate was washed with water, brine, dried over Na$_2$SO$_4$ and concentrated. Chromatography of the residue (95:5 EtOAc/MeOH) gave the title compound 20 (0.19 g, 40%) as a pale yellow viscous oil.

$^1$H NMR (CDCl$_3$): 7.40–7.18 (10H, m), 7.05 (2H, m), 6.70 (2H, m), 4.57 (1H, m), 3.60 (1H, bd), 3.40 (5H, m), 2.80 (1H, m), 2.60 (1H, m), 2.58 (2H, m), 2.20 (1H, m), 1.90 (1H, m), 1.18 (6H, bs).

$^{13}$C NMR(CDCl$_3$): 171.4, 149.3, 145.2, 138.9, 129.4, 128.4, 128.1, 128.0, 127.7, 127.2, 126.7, 125.0, 117.1, 60.3, 58.3, 57.8, 53.0, 41 (b), 29.5, 13.4.

An analytical sample was obtained as a hydrochloride by adding an etheral solution of the free base to ice cold diluted etheral HCl.

IR (neat): 3430,1610,1457 cm$^{-1}$.

Anal. calcd. for C$_{28}$H$_{33}$N$_3$O*HCl*1.3H$_2$O: C, 68.99; H, 7.24; N, 8.62.

Found: C, 68.99; H, 7.57; N, 8.62.

Example 16

Preparation of N,N-diethyl-4-(N-pyrrolidin-3-yl-anilino) Benzamide (Compound 21)

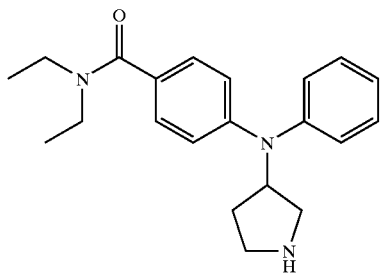

(21)

A mixture of the compound 20 (90 mg, 0.2105 mmol), $NH_4O_2CH$ (27 mg, 0.4282 mmol) and a catalytic amount of 10% Pd/C in MeOH (5 ml) was stirred vigorously at rt overnight. The catalyst was removed through celite and the filtrate condensed in vacuo to give a crude sample which was purified through MPLC (100:0 to 9:1 $CH_2Cl_2$:MeOH(10% TEA) on silica gel 60) to yield the title compound 21 (30 mg, 42%) as a pale yellow thick oil.

IR (HCl salt, film) ν: 3428 (NH), 1607($CONEt_2$) $cm^{-1}$.

$^1$H NMR (free amine, 400 MHz, $CDCl_3$) δ: 1.06 (6H, m, 2×$CH_3CH_2$), 1.90 (1H, m, ArNCHCH(CH)$CH_2$), 2.30 (1H, m, ArNCHCH(CH)$CH_2$), 2.58 (2H, m, ArNCH$CH_2CH_2$N), 2.95 (1H, m, NHCH(CH)$CH_2$), 3.23 (1H, m, NHCH(CH)$CH_2$), 3.40 (4H, bs, 2×$CH_2CH_3$), 4.70 (1H, m, ArNCH), 6.68 (2H, m, Ar), 7.02 (2H, m, Ar), 7.22 (3H, m, Ar), 7.38 (2H, m, Ar).

$^{13}$C NMR (free amine, 100 Hz, $CDCl_3$) d: 13.4, 29.7, 41.9, 54.6, 57.9, 59.3, 117.5, 125.5, 127.9, 128.0, 129.7, 144.8, 149.2, 171.2.

Elemental analysis: Calcd. for $C_{21}H_{29}N_3OCl_2 \cdot 1.5H_2O$: C, 57.66; H, 7.37; N, 9.61. Found: C, 57.86; H, 7.38; N, 9.03.

Example 17

(i) Preparation of 4-[N-(1-benzyl-piperidin-4-yl)-amino]-N,N-diethyl Benzenesulfonamide (Compound 22)

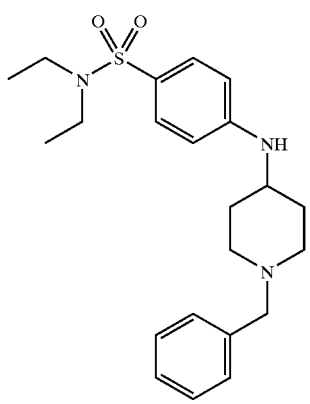

(22)

Ti(O—i—Pr)$_4$ (2.10 mL, 7.10 mmol) was added to a mixture of 4-amino-(N,N-diethyl)-benzenesulfonamide (0.81 g, 3.55 mmol) and 1-benzyl-4-piperidone (0.99 mL, 5.32 mmol) at room temperature. The mixture was sonicated at 40° C. for 40 min, and stirred at 60° C. for 18 h. The dark mixture was cooled in an ice-bath and EtOH (15 mL) followed by $NaBH_4$ pellets (0.5 g, 13.2 mmol) were added. After stirring for 1 h at 0° C. and 20 h at room temperature, 1M $NH_4OH$ (5 mL) was added. The mixture was stirred at room temperature for 30 min, diluted with $CH_2Cl_2$ (25 mL) and filtered through a pad of Celite®. The layers in the filtrate were separated, the aqueous layer extracted with $CH_2Cl_2$ (15 mL) and the combined organic phases washed with $NaHCO_3$ (aq., sat., 25 mL) and dried over $K_2CO_3$. The mixture was filtered, concentrated and the residue purified by chromatography (gradient, PhMe to $Me_2CO$) to give the title compound 22 (0.91 g, 46%) as a tan solid.

IR (KBr): 2942, 1560, 1520, 1321, 1146, 920 $cm^{-1}$.

$^1$H NMR ($CDCl_3$): 7.55 (d, 2H), 7.34–7.23 (m, 5H), 6.54 (d, 2H), 4.08 (d, 1H), 3.53 (s, 2H), 3.29 (broad s, 1H), 3.17 (q, 4H), 2.85 (d, 2H), 2.16 (t, 2H), 2.01 (d, 2H), 1.51 (q, 2H), 1.11 (t, 6H).

$^{13}$C NMR ($CDCl_3$): 150.2, 138.2, 129.1, 129.0, 128.2, 127.0, 126,8, 63.0, 52.1, 49.6, 41.9, 32.2, 14.1.

(ii) Preparation of 4-[N-(1-benzyl-piperidin-4-yl)-anilino]-N,N-diethyl Benzenesulfonamide (Compound 23)

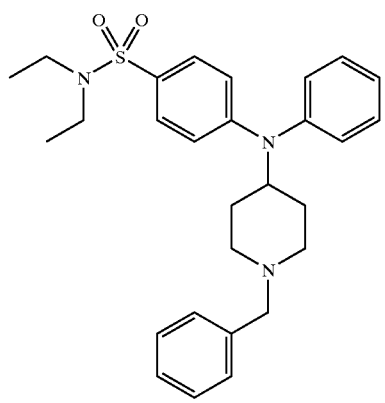

(23)

A mixture of 4-[N-(1-benzyl-piperidin-4-yl)-amino]-N,N-diethyl benzenesulfonamide (compound 22), (0.44 g, 1.10 mmol), $Ph_3Bi$ (0.58 g, 1.31 mmol) and $Cu(OAc)_2$ (0.30 g, 1.64 mmol) in PhMe (20 mL) was heated at reflux for 24 h. $Ph_3Bi$ (0.58 g, 1.31 mmol) and $Cu(OAc)_2$ (0.30 g, 1.64 mmol) were added. The mixture was stirred at reflux for 24 h and $Ph_3Bi$ (0.58 g, 1.31 mmol) and $Cu(OAc)_2$ (0.30 g, 1.64 mmol) were added. After reflux for 24 h the mixture was allowed to cool and quenched with 1M $NH_4OH$ (5 mL). The mixture was stirred at room temperature for 30 min, diluted with EtOAc (25 mL) and filtered through a pad of Celite. The layers in the filtrate were separated, the deep blue aqueous layer extracted with EtOAc (25 mL) and the combined organic phases washed with $H_2O$ (50 mL) and brine (25 mL) and dried over $K_2CO_3$. The mixture was filtered, concentrated and the residue purified by chromatography (gradient, PhMe to $Me_2CO$) to give the title compound 23 (50 mg, 10%) as a brown oil.

$^1$H NMR ($CDCl_3$): 7.51 (d, 2H), 7.43 (t, 2H), 7.35 (t, 1H), 7.30–7.22 (m, 5H), 7.07 (d, 2H), 6.48 (d, 2H), 3.86 (t, 1H), 3.48 (s, 2H), 3.18 (q, 4H), 2.94 (d, 2H), 2.11 (t, 2H), 1.91 (d, 2H), 1.50 (q, 2H), 1.11 (t, 6H).

$^{13}$C NMR (CDCl$_3$): 151.8, 141.5, 138.1, 131.1, 129.9, 129.1, 128.6, 128.1, 127.5, 127.0, 125.9, 112.7, 63.0, 55.8, 53.1, 42.0, 30.6, 14.2.

Purification with HPLC (LiChroPrep RP-18, eluation with increasing amounts of 0.1% TFA/MeCN in 0.1% TFA/H$_2$O) gave an analytical sample as a white solid.

IR (KBr): 3433, 1677, 1586, 1496, 1324, 1196, 1148, 719 cm$^{-1}$.

Anal. calcd. for C$_{28}$H$_{35}$N$_3$O$_2$S*1.25 CF$_3$COOH: C, 59.07; H, 5.89; N, 6.78.

Found: C, 59.00; H, 6.01; N, 7.01.

Example 18

Preparation of N,N-diethyl-4-(N-piperidin-4-yl-anilin) Benzenesulfonamide (Compound 24)

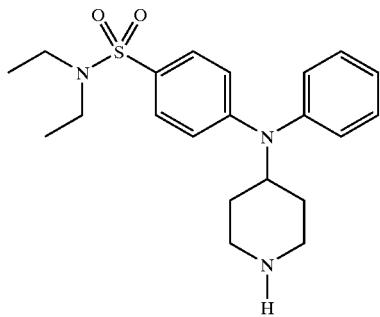

(24)

(1-chloroethyl) chloroformate (10 μL, 0.1 mmol) was added to a solution of 4-[N-(1-benzyl-piperidin-4-yl)-anilino]-N,N-diethyl benzenesulfonamide (compound 23) (19 mg, 40 μmol) in toluene (1 mL) at room temperature. The mixture was heated at reflux for 16 h, allowed to cool to room temperature and concentrated. Methanol (1 mL) was added and the mixture was heated at reflux for 4 h, allowed to cool and concentrated. The residue was partitioned between CH$_2$Cl$_2$ (5 ML) and 1M NH$_4$OH (5 mL). The layers were separated and the organic phase was washed with H$_2$O (5 mL) and brine (5 mL) and dried over K$_2$CO$_3$. The mixture was filtered, concentrated and the residue purified by HPLC (LiChroPrep RP-18, eluation with increasing amounts of 0.1% TFA/MeCN in 0.1% TFA/H$_2$O) to give the title compound 24 (13 mg, 84%) as the trifluoroacetate.

IR (KBr): 3420, 1658, 1199, 1146, 714 cm$^{-1}$.

$^1$H NMR (CD$_3$OD: δ: 7.66–7.63 (m, 4H), 7.55 (t, 1H), 7.28 (d, 2H), 6.76 (d, 2H), 4.50 (t, 1H), 3.54 (d, 2H), 3.35–3.23 (m, 6H), 2.34 (d, 2H), 1.73 (q, 2H), 1.19 (t, 6H).

$^{13}$C NMR (CD$_3$OD) δ: 153.4, 142.4, 132.8, 131.7, 130.1, 129.7, 128.8, 114.4, 53.6, 45.2, 43.6, 29.2, 14.9.

Anal. calcd. for CH$_{28}$H$_{35}$N$_3$O$_2$S×2 CF$_3$COOH×1.5H$_2$O: C, 46.73; H, 5.33; N, 6.54

Found: C, 46.54; H, 5.01; N, 6.71

The best mode of performing the invention known at present, is to use the compounds of Example 1,2,3,4,5,6,7, 17 and 18.

Pharmaceutical Compositions

The novel compounds according to the present invention may be administered orally, intramuscularly, subcutaneously, topically, intranasally, intraperitoneally, intrathoracially, intravenously, epidurally, intrathecally, intracerebroventricularly and by injection into the joints.

A preferred route of administration is orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminium, calcium, lithium, magnesium, potassium, sodium, and zinc.

Preferred pharmaceutically acceptable salts are the hydrochlorides, trifluoroacetates and bitartrates.

The term composition is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Biological Evaluation

A) In Vitro Model

Cell Culture

Human 293S cells expressing cloned human $\mu$, $\delta$, and $\kappa$ receptors and neomycin resistance were grown in suspension at 37° C. and 5% $CO_2$ in shaker flasks containing calcium-free DMEM10% FBS, 5% BCS, 0.1% Pluronic F-68, and 600 $\mu$g/ml geneticin.

Membrane Preparation

Cells were pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension was spun at 1000 g (max) for 10 min at 4° C. The supernatant was saved on ice and the pellets resuspended and spun as before. The supernatants from both spins were combined and spun at 46,000 g(max) for 30 min. The pellets were resuspended in cold Tris buffer (50 mM Tris/Cl, pH 7.0) and spun again. The final pellets were resuspended in membrane buffer (50 mM Tris, 0.32 M sucrose, pH 7.0). Aliquots (1 ml) in polypropylene tubes were frozen in dry ice/ethanol and stored at −70° C. until use. The protein concentrations were determined by a modified Lowry assay with SDS.

Binding Assays

Membranes were thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which was stored at 4° C. after filtration through a 0.22 m filter, and to which had been freshly added 5 $\mu$g/ml aprotinin, 10 $\mu$M bestatin, 10 $\mu$M diprotin A, no DTT). Aliquots of 100 $\mu$l (for $\mu$g protein, see Table 1) were added to iced 12×75 mm polypropylene tubes containing 100 $\mu$l of the appropriate radioligand (see Table 1) and 100 $\mu$l of test peptides at various concentrations. Total (TB) and nonspecific (NS) binding were determined in the absence and presence of 10 $\mu$M naloxone respectively. The tubes were vortexed and incubated at 25° C. for 60–75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters was measured with a beta counter after soaking the filters for at least 12 h in minivials containing 6–7 ml scintillation fluid. If the assay is set up in 96-place deep well plates, the filtration is over 96-place PEI-soaked unifilters, which were washed with 3×1 ml wash buffer, and dried in an oven at 55° C. for 2 h. The filter plates were counted in a TopCount (Packard) after adding 50 $\mu$l MS-20 scintillation fluid/well.

Data Analysis

The specific binding (SB) was calculated as TB-NS, and the SB in the presence of various test peptides was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$; and $n_H$ were reported for ligands tested in at least three displacement curves.

Receptor Saturation Experiments

Radioligand $K_\delta$ values were determined by performing the binding assays on cell membranes with the appropriate radioligands at concentrations ranging from 0.2 to 5 times the estimated $K_\delta$ (up to 10 times if amounts of radioligand required are feasable). The specific radioligand binding was expressed as pmole/mg membrane protein. Values of K$\delta$ and Bmax from individual experiments were obtained from nonlinear fits of specifically bound (B) vs. nM free (F) radioligand from individual according to a one-site model.

B) Biological Model (In Vivo Model)

Freund's Complete Adjuvant (FCA), and Sciatic Nerve Cuff Induced Mechano-Allodynia in Rat Animals Male Sprague-Dawley rats (Charles River, St-Constant, Canada) weighing 175–200 g at the time of surgery were used. They were housed in groups of three in rooms thermostatically maintained at 20° C. with a 12:12 hr light/dark cycle, and with free access to food and water. After arrival, the animals were allowed to acclimatize for at least 2 days before surgery. The experiments were approved by the appropriate Medical Ethical Committee for animal studies.

Experimental Procedure

Freund's Complete Adjuvant

The rats were first anesthetized in a Halothane chamber after which 10 $\mu$l of FCA was injected s.c. into the dorsal region of the left foot, between the second and third external digits. The animals were then allowed to recover from anesthesia under observation in their home cage.

Sciatic Nerve Cuff

The animals were prepared according to the method described by Mosconi and Kruger (1996). Rats were anesthetized with a mixture of Ketamine/Xylazine i.p. (2 ml/kg) and placed on their right side and an incision made over, and along the axis of, the lateral aspect of the left femur. The muscles of the upper quadriceps were teased apart to reveal the sciatic nerve on which a plastic cuff (PE-60 tubing, 2 mm long) was placed around. The wound was then closed in two layers with 3-0 vicryl and silk sutures.

Determination of Mechano-Allodynia Using Von Frey Testing

Testing was performed between 08:00 and 16:00 h using the method described by Chaplan et al. (1994). Rats were placed in Plexiglas cages on top of a wire mesh bottom which allowed access to the paw, and were left to habituate for 10–15 min. The area tested was the mid-plantar left hind paw, avoiding the less sensitive foot pads. The paw was touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair was applied from underneath the mesh floor perpendicular to the plantar surface with sufficient force to cause a slight buckling against the paw, and held for approximately 6–8 seconds. A positive response was noted if the paw was sharply withdrawn. Flinching immediately upon removal of the hair was also considered a positive response. Ambulation was considered an ambiguous response, and in such cases the stimulus was repeated.

Testing Protocol

The animals were tested on postoperative day 1 for the FCA-treated group and on postoperative day 7 for the Sciatic Nerve Cuff group. The 50% withdrawal threshold was determined using the up-down method of Dixon (1980). Testing was started with the 2.04 g hair, in the middle of the series. Stimuli were always presented in a consecutive way, whether ascending or descending. In the absence of a paw withdrawal response to the initially selected hair, a stronger stimulus was presented; in the event of paw withdrawal, the next weaker stimulus was chosen. Optimal threshold calculation by this method requires 6 responses in the immediate vicinity of the 50% threshold, and counting of these 6 responses began when the first change in response occurred, e.g. the threshold was first crossed. In cases where thresholds fell outside the range of stimuli, values of 15.14 (normal sensitivity) or 0.41 (maximally allodynic) were respectively assigned. The resulting pattern of positive and negative responses was tabulated using the convention, X=no withdrawal; O=withdrawal, and the 50% withdrawal threshold was interpolated using the formula:

$$50\% \ g \ \text{threshold} = 10^{(Xf+k\delta)}/10{,}000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds were converted to percent of maximum possible effect (% MPE), according to Chaplan et al. 1994. The following equation was used to compute % MPE:

$$\% \ \text{MPE} = \frac{\text{Drug treated threshold (g)} - \text{allodynia threshold (g)}}{\text{Control threshold (g)} - \text{allodynia threshold (g)}} \times 100$$

Administration of Test Substance

Rats were injected (subcutaneously, intraperitoneally, or orally) with a test substance prior to von Frey testing, the time between administration of test compound and the von Frey test varied depending upon the nature of the test compound.

What is claimed is:

1. A compound of the formula (I)

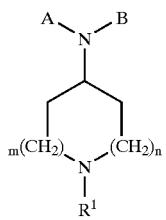

wherein
m is 1;
n is 1;
$R^1$ is selected from
hydrogen;
a branched or straight $C_1$–$C_6$ alkyl;
$C_3$–$C_8$ cycloalkyl;
$C_4$–$C_8$(alkyl-cycloalkyl) wherein alkyl is $C_1$–$C_2$ alkyl and cycloalkyl is $C_3$–$C_6$ cycloalkyl;
benzyl;

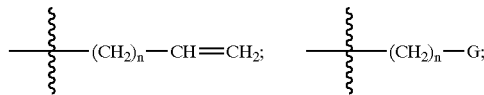

where G is a hydroaromatic or a heteroaromatic group having 5 or 6 atoms, and where the heteroatoms are selected from O, S and N; and

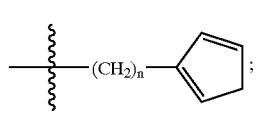

and wherein n=0 or 1;
$C_6$–$C_{10}$ aryl; or heteroaryl having from 5 to 10 atoms selected from any of C, S, N and O; wherein the aryl and heteroaryl may optionally and independently be substituted by 1 or 2 substituents independently selected from any of hydrogen, $CH_3$, $(CH_2)_pCF_3$, halogen, $CONR^5R^4$, $COOR^5$, $COR^5$, $(CH_2)_pNR^5R^4$, $(CH_2)_p CH_3(CH_2)_pSOR^5R^4$, $(CH_2)_pSO_2R^5$, and $(CH_2)_p SO_2NR^5$, wherein $R^4$ and $R^5$ are each independently as defined below and p is 0, 1 or 2;

($C_1$–$C_2$ alkyl)-($C_6$–$C_{10}$ aryl); or ($C_1$–$C_2$ alkyl)heteroaryl, the heteroaryl moieties having from 5 to 10 atoms selected from any of C, S, N and O, and where the aryl or heteroaryl may optionally and independently be substituted by 1 or 2 substituents independently selected from any of hydrogen, $CH_3$, $CONR^5R^4$, $COOR^5$, $COR^5$, $(CH_2)_qNR^5R^4$, $(CH_2)_qCH_3$ $(CH_2)_q SOR^5R^4$, $(CH_2)_qSO_2R^5$, $(CH_2)_qSO_2NR^5$, and $(CH_2)_q OR^4$, wherein $R^4$ and $R^5$ are each independently as defined below and q is 0, 1 or 2;

A is

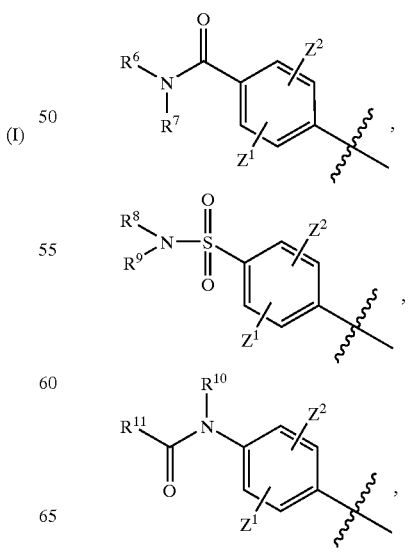

-continued

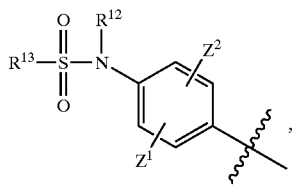

and

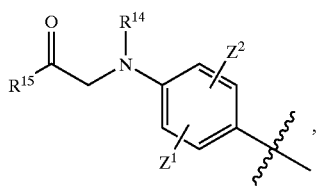

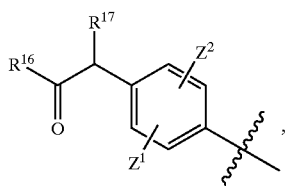

and

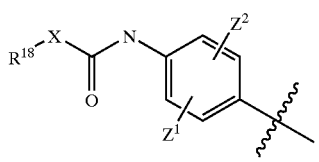

wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are each independently as defined below and wherein the phenyl ring of each A substituent may be optionally and independently substituted by 1 or 2 substituents $Z^1$ and $Z^2$ which are each and independently selected from hydrogen, $CH_3$, $(CH_2)_rCF_3$, halogen, $CONR^2R^3$, $CO_2R^2$, $COR^2$, $(CH_2)_rNR^2R^3$, $(CH_2)_rCH_3(CH_2)_rSOR^2$, $(CH^2)_rSO_2R^2$ and $(CH_2)_rSO_2NR^2R^3$ wherein $R^2$ and $R^3$ are each independently as defined below and wherein r is 0, 1 or 2; X is O, S or $NR^{19}$ where $R^{19}$ is as defined below;

B is a substituted or unsubstituted aromatic, heteroaromatic, hydroaromatic or heterohydroaromatic moiety having from 5 to 10 atoms selected from any of C, S, N an O, optionally and independently substituted by 1 or 2 substituents independently selected from hydrogen, $CH_3$, $(CH_2)_rCF_3$, halogen, $(CH_2)_tCONR^5R^4$, $(CH_2)_rNR^5R^4$, $(CH_2)_tCOR^5$, $(CH_2)_tCOOR^5$, $OR^5$, $(CH_2)_rSOR^5$, $(CH_2)_tSO_2R^5$, and $(CH_2)_tSO_2NR^5R^4$, wherein $R^4$ and $R^5$ are each independently as defined below and t is 0, 1, 2 or 3;

wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are selected from:

hydrogen;

a branched or straight $C_1$–$C_6$ alkyl;

$C_3$–$C_8$ cycloalkyl;

$C_4$–$C_8$(alkyl-cycloalkyl) wherein alkyl is $C_1$–$C_2$ alkyl and cycloalkyl is $C_3$–$C_6$ cycloalkyl;

benzyl;

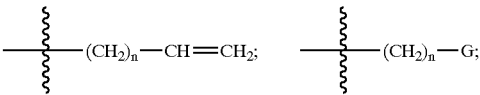

where G is a hydroaromatic or a heteroaromatic group having 5 or 6 atoms, and where the heteroatoms are selected from O, S and N; and

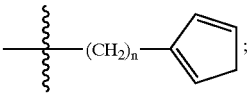

wherein n=0 or 1;

$C_6$–$C_{10}$ aryl; or heteroaryl having from 5 to 10 atoms selected from any of C, S, N and O; wherein the aryl and heteroaryl may optionally and independently be substituted by 1 or 2 substituents independently selected from any of hydrogen, $CH_3$, $(CH_2)_pCF_3$, and halogen and p is 0, 1 or 2;

($C_1$–$C_2$ alkyl)-($C_6$–$C_{10}$ aryl); or ($C_1$–$C_2$ alkyl)heteroaryl, the heteroaryl moieties having from 5 to 10 atoms selected from any of C, S, N and O, and where the aryl or heteroaryl may optionally and independently be substituted by 1 or 2 substituents independently selected from any of hydrogen, and $CH_3$;

or the pharmaceutically acceptable salt, isomer, hydrate, isoform or prodrug thereof.

2. The compound of claim 1, wherein:

$R^1$ is selected from benzyl;

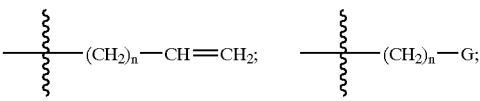

where G is a hydroaromatic or a heteroaromatic group having 5 or 6 atoms, and where the heteroatoms are selected from O, S and N; and

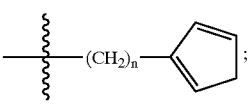

and wherein n=0 or 1;

A is selected from any one of

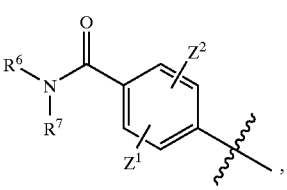

-continued

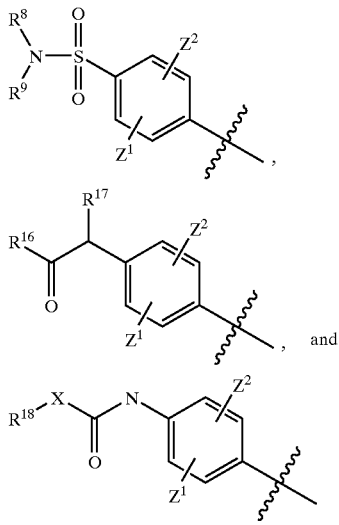

wherein $R^6$, $R^7$, $R^8$, $R^9$, $R^{16}$, $R^{17}$ and $R^{18}$ are each independently as defined below;

B is selected from phenyl, naphthyl, indolyl, benzofuranyl, dihydrobenzofuranyl, benzothiophenyl, pyrroyl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, terahydrofuranyl, pyrrolidinyl, and indazolinyl, each optionally and independently substituted by 1 or 2 substituents independently selected from hydrogen, $CH_3$, $CF_3$, halogen, $-(CH_2)_tCONR^5R^4$, $-(CH_2)_tNR^5R^4$, $-CH_2)_tCOR^5$, $-(CH_2)_tCO_2R^5$, and $-OR^5$, wherein t is 0 or 1, and wherein $R^4$ and $R^5$ are as defined below;

wherein $R^4$ and $R^5$, $R^6$, $R^7$, $R^8$, $R^9$, $R^{16}$, $R^{17}$ and $R^{18}$ are each independently selected from:

hydrogen;

a branched or straight $C_1$–$C_6$ alkyl;

$C_3$–$C_8$ cycloalkyl;

$C_4$–$C_8$(alkyl-cycloalkyl) wherein alkyl is $C_1$–$C_2$ alkyl and cycloalkyl is $C_3$–$C_6$ cycloalkyl;

benzyl;

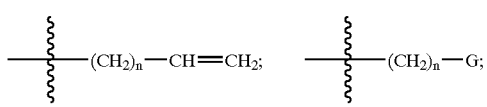

where G is a hydroaromatic or a heteroaromatic group having 5 or 6 atoms, and where the heteroatoms are selected from O, S and N; and

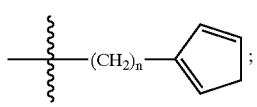

and wherein n=0 or 1.

3. The compound of claim 1, wherein
$R^1$ is ($C_1$–$C_2$ alkyl)phenyl or hydrogen;

A is

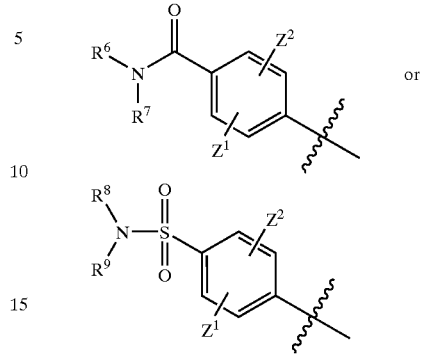

or wherein $R^6$, $R^7$, $R^8$, $R^9$, is each an ethylene group; and $Z^1$ and $Z^2$, are as defined in claim 1;

B is phenyl or naphthalene.

4. The compound of claim 1, wherein A is:

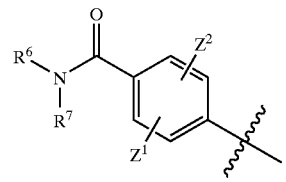

5. The compound of claim 4, wherein $Z^1$ and $Z^2$ are both hydrogen.

6. The compound of claim 5, wherein $R^6$ and $R^7$ are each a branched or straight $C_1$–$C_6$ alkyl.

7. The compound of claim 6, wherein $R^6$ and $R^7$ are each a straight $C_1$–$C_3$ alkyl.

8. The compound of claim 7, wherein $R^6$ and $R^7$ are each an ethyl.

9. The compound of claim 1, wherein B is an aromatic optionally and independently substituted by 1 or 2 substituents independently selected from hydrogen, $CH_3(CH_2)_tCF_3$, halogen, $(CH_2)_tCONR^5R^4$, $(CH_2)$ $NR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_t$ $SO_2NR^5R^4$, wherein $R^4$ and $R^5$ are each and independently as defined in claim 1 and t is 0, 1, 2 or 3.

10. The compound of claim 9, wherein B is a phenyl optionally substituted with one or two substituents each and independently selected from hydrogen, $CH_3(CH_2)_tCF_3$, halogen, $(CH_2)_tCONR^5R^4$, $(CH_2)_tNR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_t$ $SO_2NR^5R^4$.

11. The compound of claim 10, wherein B is unsubstituted.

12. The compound of claim 11, wherein A is:

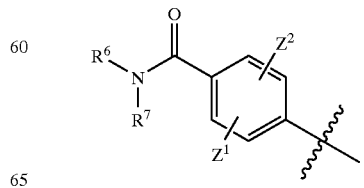

13. The compound of claim 12, wherein $Z^1$ and $Z^2$ are both hydrogen.

14. The compound of claim 13, wherein $R^6$ and $R^7$ are each a branched or straight $C_1$–$C_6$ alkyl.

15. The compound of claim 14, wherein $R^6$ and $R^7$ are each a straight $C_1$–$C_3$ alkyl.

16. The compound of claim 15, wherein $R^6$ and $R^7$ are each an ethyl.

17. The compound of claim 1, wherein $R^1$ is a ($C_1$–$C_2$ alkyl)-($C_6$–$C_{10}$ aryl); optionally substituted by 1 or 2 substituents independently selected from any of hydrogen, $CH_3$, $CONR^5R^4$, $COOR^5$, $COR^5$, $(CH_2)_q NR^5R^4$, $(CH_2)_q CH_3$ $(CH_2)_q SOR^5R^4$, $(CH_2)_q SO_2R^5$, $(CH_2)_q SO_2NR^5$, and $(CH_2)_q OR^4$, wherein $R^4$ and $R^5$ are each independently as defined in claim 1 and q is 0, 1 or 2.

18. The compound of claim 17, wherein the aryl in said ($C_1$–$C_2$ alkyl)-($C_6$–$C_{10}$ aryl) is unsubstituted.

19. The compound of claim 18, wherein said ($C_1$–$C_2$ alkyl)-($C_6$–$C_{10}$ aryl) is a ($C_1$–$C_2$ alkyl)-phenyl.

20. The compound of claim 19, wherein B is an aromatic optionally and independently substituted by 1 or 2 substituents independently selected from hydrogen, $CH_3(CH_2)_t CF_3$, halogen, $(CH_2)_t CONR^5R^4$, $(CH_2)_t NR^5R^4$, $(CH_2)_t COR^5$, $(CH_2)_t COOR^5$, $OR^5$, $(CH_2)_t SOR^5$, $(CH_2)_t SO_2R^5$, and $(CH_2)_t SO_2NR^5R^4$.

21. The compound of claim 20, wherein B is a phenyl optionally substituted with one or two substituents each and independently selected from hydrogen, $CH_3(CH_2)_t CF_3$, halogen, $(CH_2)_t CONR^5R^4$, $(CH_2)_t NR^5R^4$, $(CH_2)_t COR^5$, $(CH_2)_t COOR^5$, $OR^5$, $(CH_2)_t SOR^5$, $(CH_2)_t SO_2R^5$, and $(CH_2)_t SO_2NR^5R^4$.

22. The compound of claim 21, wherein B is unsubstituted.

23. The compound of claim 19, wherein A is:

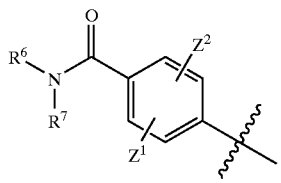

24. The compound of claim 23, wherein $Z^1$ and $Z^2$ are both hydrogen.

25. The compound of claim 24, wherein $R^6$ and $R^7$ are each a branched or straight $C_1$–$C_6$ alkyl.

26. The compound of claim 25, wherein $R^6$ and $R^7$ are each a straight $C_1$–$C_3$ alkyl.

27. The compound of claim 26, wherein $R^6$ and $R^7$ are each an ethyl.

28. The compound of claim 22, wherein A is:

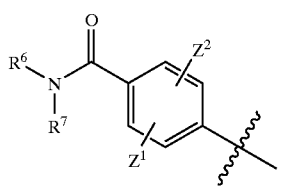

29. The compound of claim 28, wherein $Z^1$ and $Z^2$ are both hydrogen.

30. The compound of claim 29, wherein $R^6$ and $R^7$ are each a branched or straight $C_1$–$C_6$ alkyl.

31. The compound of claim 30, wherein $R^6$ and $R^7$ are each a straight $C_1$–$C_3$ alkyl.

32. The compound of claim 31, wherein $R^6$ and $R^7$ are each an ethyl.

33. The compound of claim 1 wherein said compound has the structure:

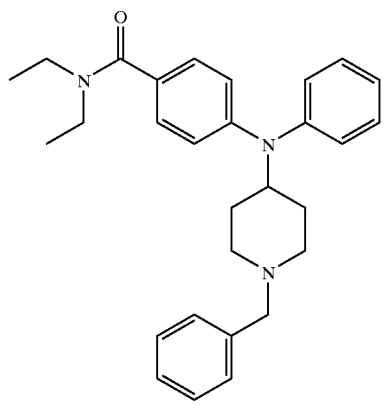

34. The compound of claim 1, wherein said compound is in the form of a hydrochloride, bitartrate or trifluoroacetate salt.

35. A pharmaceutical composition comprising a therapeutically effective amount of a compound according to any one of claims 1, 8, 11, 16, 19, 22, 27, 32 or 33 as an active ingredient, together with a pharmaceutically acceptable carrier.

36. A method of treating a patient for pain, comprising administering a compound according to any one of claims 1, 8, 11, 16, 19, 22, 27, 32 or 33 to said patient at a dosage sufficient to reduce or eliminate said pain.

37. A compound of the formula (I)

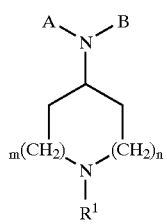

(I)

wherein
m is 0;
n is 1;
$R^1$ is selected from
  hydrogen;
  a branched or straight $C_1$–$C_6$ alkyl;
  $C_3$–$C_8$ cycloalkyl;
  $C_4$–$C_8$(alkyl-cycloalkyl) wherein alkyl is $C_1$–$C_2$ alkyl and cycloalkyl is $C_3$–$C_6$ cycloalkyl;
  benzyl;

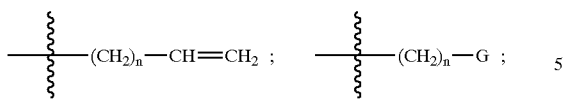

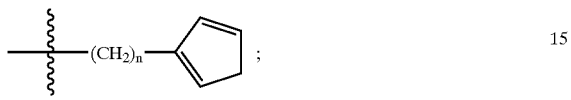

where G is a hydroaromatic or a heteroaromatic group having 5 or 6 atoms, and where the heteroatoms are selected from O, S and N; and and wherein n=0 or 1;

$C_6$–$C_{10}$ aryl; or heteroaryl having from 5 to 10 atoms selected from any of C, S, N and O; wherein the aryl and heteroaryl may optionally and independently be substituted by 1 or 2 substituents independently selected from any of hydrogen, $CH_3$, $(CH_2)_pCF_3$, halogen, $CONR^5R^4$, $COOR^5$, $COR^5$, $(CH_2)_pNR^5R^4$, $(CH_2)_p CH_3(CH_2)_p SOR^5R^4$, $(CH_2)_pSO_2R^5$, and $(CH_2)_p SO_2NR^5$, wherein $R^4$ and $R^5$ are each independently as defined below and p is 0, 1 or 2;

($C_1$–$C_2$ alkyl)-($C_6$–$C_{10}$ aryl); or ($C_1$–$C_2$ alkyl)heteroaryl, the heteroaryl moieties having from 5 to 10 atoms selected from any of C, S, N and O, and where the aryl or heteroaryl may optionally and independently be substituted by 1 or 2 substituents independently selected from any of hydrogen, $CH_3$, $CONR^5R^4$, $COOR^5$, $COR^5$, $(CH_2)_qNR^5R^4$, $(CH_2)_qCH_3$ $(CH_2)_q SOR^5R^4$, $(CH_2)_qSO_2R^5$, $(CH_2)_qSO_2NR^5$, and $(CH_2)_q OR^4$, wherein $R^4$ and $R^5$ are each independently as defined below and q is 0, 1 or 2;

A is

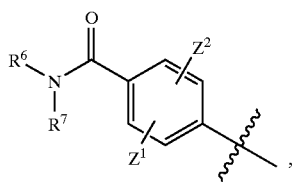
,

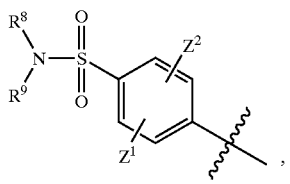
,

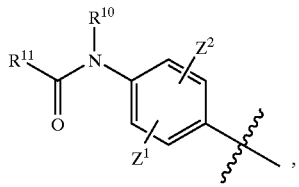
,

-continued

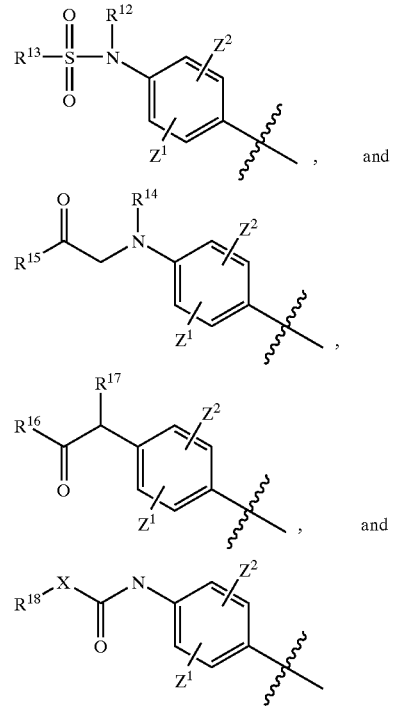

wherein $R^6$, $R^7$, $R^8$, $R^9$, $R^{10}$, $R^{11}$, $R^{22}$, $R^{13}$, $R^{14}$, $R^{15}$, $R^{16}$, $R^{17}$, and $R^{18}$ are each independently as defined below and wherein the phenyl ring of each A substituent may be optionally and independently substituted by 1 or 2 substituents $Z^1$ and $Z^2$ which are each and independently selected from hydrogen, $CH_3$, $(CH_2)_rCF_3$, halogen, $CONR^2R^3$, $CO_2R^2$, $COR^2$, $(CH_2)_rNR^2R^3$, $(CH_2)_rCH_3(CH_2)_rSOR^2$, $(CH^2)_rSO_2R^2$ and $(CH_2)_rSO_2NR_2R^1$ wherein $R^2$ and $R^3$ are each independently as defined below and wherein r is 0, 1 or 2; X is O, S or $NR^{19}$ where $R^{19}$ is as defined below;

B is a substituted or unsubstituted aromatic, heteroaromatic, hydroaromatic or heterohydroaromatic moiety having from 5 to 10 atoms selected from any of C, S, N an O, optionally and independently substituted by 1 or 2 substituents independently selected from hydrogen, $CH_3$, $(CH_2)_tCF_3$, halogen, $(CH_2)_tCONR^5R^4$, $(CH_2)_tNR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_tSO_2NR^5R^4$, wherein $R^4$ and $R^5$ are each independently as defined below and t is 0, 1, 2 or 3;

wherein $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ are selected from hydrogen;

a branched or straight $C_1$–$C_6$ alkyl;

$C_3$–$C_8$ cycloalkyl;

$C_4$–$C_8$(alkyl-cycloalkyl) wherein alkyl is $C_1$–$C_2$ alkyl and cycloalkyl is $C_3$–$C_6$ cycloalkyl;

benzyl;

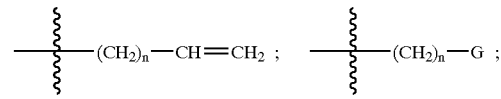

where G is a hydroaromatic or a heteroaromatic group having 5 or 6 atoms, and where the heteroatoms are selected from O, S and N; and

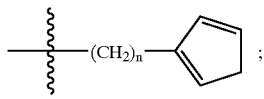

and wherein n=0 or 1;

$C_6$–$C_{10}$ aryl; or heteroaryl having from 5 to 10 atoms selected from any of C, S, N and O; wherein the aryl and heteroaryl may optionally and independently be substituted by 1 or 2 substituents independently selected from any of hydrogen, $CH_3$, $(CH_2)_pCF_3$, and halogen and p is 0, 1 or 2;

$(C_1$–$C_2$ alkyl)-$(C_6$–$C_{10}$ aryl); or $(C_1$–$C_2$ alkyl)heteroaryl, the heteroaryl moieties having from 5 to 10 atoms selected from any of C, S, N and O, and where the aryl or heteroaryl may optionally and independently be substituted by 1 or 2 substituents independently selected from any of hydrogen, and $CH_3$;

or the pharmaceutically acceptable salt, isomer, hydrate, isoform or prodrug thereof.

38. The compound of claim 37, wherein $R^1$ is selected from benzyl;

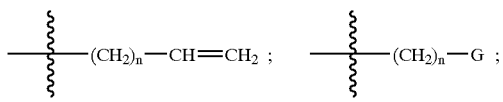

where G is a hydroaromatic or a heteroaromatic group having 5 or 6 atoms, and where the heteroatoms are selected from O, S and N; and

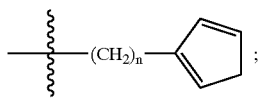

and wherein n=0 or 1;

A is selected from any one of

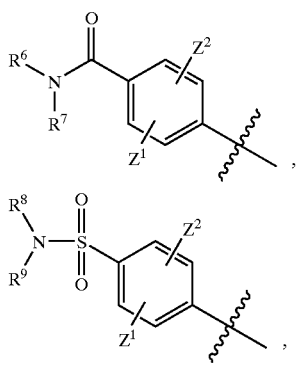

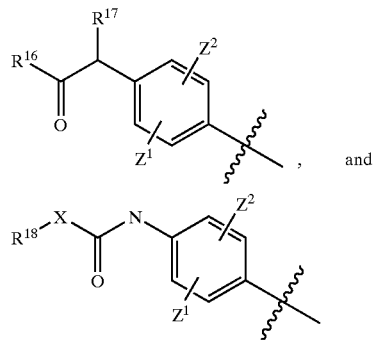

wherein $R^6$, $R^7$, $R^8$, $R^9$, $R^{16}$, $R^{17}$ and $R^{18}$ are each independently as defined below;

B is selected from phenyl, naphthyl, indolyl, benzofuranyl, dihydrobenzofuranyl, benzothiophenyl, pyrroyl, furanyl, quinolinyl, isoquinolinyl, cyclohexyl, cyclohexenyl, cyclopentyl, cyclopentenyl, indanyl, indenyl, tetrahydronaphthyl, tetrahydroquinyl, tetrahydroisoquinolinyl, terahydrofuranyl, pyrrolidinyl, and indazolinyl, each optionally and independently substituted by 1 or 2 substituents independently selected from hydrogen, $CH_3$, $CF_3$, halogen, —$(CH_2)_tCONR^5R^4$, —$(CH_2)_tNR^5R^4$, —$CH_2)_tCOR^5$, $(CH_2)_tCO_2R^5$, and —$OR^5$;

wherein t is 0 or 1, and wherein $R^4$ and $R^5$ are as defined below;

wherein $R^4$ and $R^5$, $R^6$, $R^7$, $R^8$, $R^9$, $R^{16}$, $R^{17}$ and $R^{18}$ are each independently selected from:

hydrogen;

a branched or straight $C_1$–$C_6$ alkyl;

$C_3$–$C_8$ cycloalkyl;

$C_4$–$C_8$(alkyl-cycloalkyl) wherein alkyl is $C_1$–$C_2$ alkyl and cycloalkyl is $C_3$–$C_6$ cycloalkyl;

benzyl;

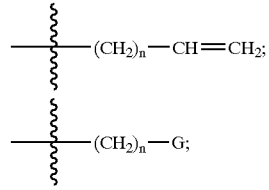

where G is a hydroaromatic or a heteroaromatic group having 5 or 6 atoms, and where the heteroatoms are selected from O, S and N; and

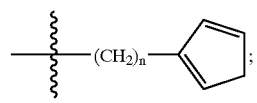

and wherein n=0 or 1.

39. The compound of claim 37, wherein $R^1$ is $(C_1$–$C_2$ alkyl)phenyl or hydrogen;

A is

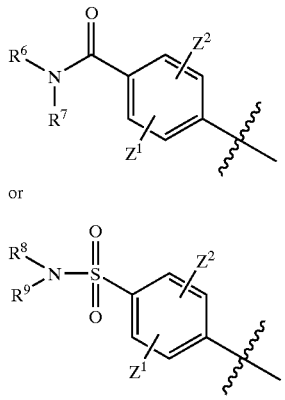

or wherein $R^6$, $R^7$, $R^8$, $R^9$, is each an ethylene group;
a B is phenyl or naphthalene.

40. The compound of claim 37, wherein A is:

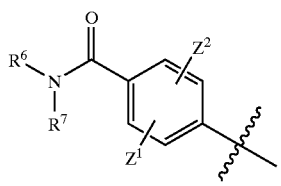

41. The compound of claim 40, wherein $Z^1$ and $Z^2$ are both hydrogen.

42. The compound of claim 41, wherein $R^6$ and $R^7$ are each a branched or straight $C_1$–$C_6$ alkyl.

43. The compound of claim 42, wherein $R^6$ and $R^7$ are each a straight $C_1$–$C_3$ alkyl.

44. The compound of claim 43, wherein $R^6$ and $R^7$ are each an ethyl.

45. The compound of claim 37, wherein B is an aromatic optionally and independently substituted by 1 or 2 substituents independently selected from hydrogen, $CH_3(CH_2)_tCF_3$, halogen, $(CH_2)_tCONR^5R^4$, $(CH_2)_tNR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_t SO_2NR^5R^4$, wherein $R^4$ and $R^5$ are each and independently as defined in claim 1 and t is 0, 1, 2 or 3.

46. The compound of claim 45, wherein B is a phenyl optionally substituted with one or two substituents each and independently selected from hydrogen, $CH_3(CH_2)_tCF_3$, halogen, $(CH_2)_tCONR^5R^4$, $(CH_2)_tNR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_t SO_2NR^5R^4$.

47. The compound of claim 46, wherein B is unsubstituted.

48. The compound of claim 47, wherein A is:

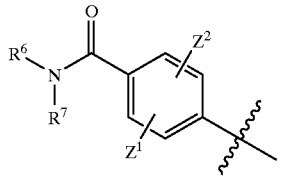

49. The compound of claim 48, wherein $Z^1$ and $Z^2$ are both hydrogen.

50. The compound of claim 49, wherein $R^6$ and $R^7$ are each a branched or straight $C_1$–$C_6$ alkyl.

51. The compound of claim 50, wherein $R^6$ and $R^7$ are each a straight $C_1$–$C_3$ alkyl.

52. The compound of claim 51, wherein $R^6$ and $R^7$ are each an ethyl.

53. The compound of claim 37, wherein $R^1$ is a $(C_1$–$C_2$ alkyl)-$(C_6$–$C_{10}$ aryl); optionally substituted by 1 or 2 substituents independently selected from any of hydrogen, $CH_3$, $CONR^5R^4$, $COOR^5$, $COR^5$, $(CH_2)_qNR^5R^4$, $(CH_2)_qCH_3$ $(CH_2)_qSOR^5R^4$, $(CH_2)_qSO_2R^5$, $(CH_2)_qSO_2NR^5$, and $(CH_2)_q OR^4$.

54. The compound of claim 53, wherein the aryl in said $(C_1$–$C_2$ alkyl)-$(C_6$–$C_{10}$ aryl) is unsubstituted.

55. The compound of claim 54, wherein said $(C_1$–$C_2$ alkyl)-$(C_6$–$C_{10}$ aryl) is a $(C_1$–$C_2$ alkyl)-phenyl.

56. The compound of claim 55, wherein B is an aromatic optionally and independently substituted by 1 or 2 substituents independently selected from hydrogen, $CH_3(CH_2)_tCF_3$, halogen, $(CH_2)_tCONR^5R^4$, $(CH_2)_tNR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_t SO_2NR^5R^4$.

57. The compound of claim 56, wherein B is a phenyl optionally substituted with one or two substituents each and independently selected from hydrogen, $CH_3(CH_2)_tCF_3$, halogen, $(CH_2)_tCONR^5R^4$, $(CH_2)_tNR^5R^4$, $(CH_2)_tCOR^5$, $(CH_2)_tCOOR^5$, $OR^5$, $(CH_2)_tSOR^5$, $(CH_2)_tSO_2R^5$, and $(CH_2)_t SO_2NR^5R^4$.

58. The compound of claim 57, wherein B is unsubstituted.

59. The compound of claim 55, wherein A is:

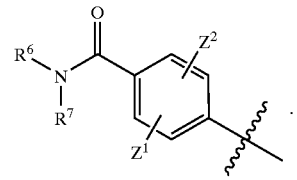

60. The compound of claim 59 wherein $Z^1$ and $Z^2$ are both hydrogen.

61. The compound of claim 60, wherein $R^6$ and $R^7$ are each a branched or straight $C_1$–$C_6$ alkyl.

62. The compound of claim 61, wherein $R^6$ and $R^7$ are each a straight $C_1$–$C_3$ alkyl.

63. The compound of claim 62, wherein $R^6$ and $R^7$ are each an ethyl.

64. The compound of claim 58, wherein A is:

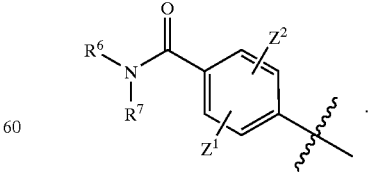

65. The compound of claim 64, wherein $Z^1$ and $Z^2$ are both hydrogen.

66. The compound of claim 65, wherein $R^6$ and $R^7$ are each a branched or straight $C_1$–$C_6$ alkyl.

67. The compound of claim 66, wherein $R^6$ and $R^7$ are each a straight $C_1$–$C_3$ alkyl.

68. The compound of claim 67, wherein $R^6$ and $R^7$ are each an ethyl.

69. The compound of claim 37, wherein said compound is in the form of a hydrochloride, bitartrate or trifluoroacetate salt.

70. A pharmaceutical composition comprising a therapeutically effective amount of a compound according to any one of claims 37, 44, 47, 52, 55, 58, 63, or 68 an active ingredient, together with a pharmaceutically acceptable carrier.

71. A method of treating a patient for pain, comprising administering a compound according to any one of claims 37, 44, 47, 52, 55, 58, 63 or 68 to said patient at a dosage sufficient to reduce or eliminate said pain.

72. A process for the preparation of a compound according to either claim 1 comprising:
(a) subjecting a ketone of the formula (IV)

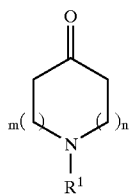

(IV)

wherein $R^1$ is as defined in claim 1, m=1, and n=1, to reductive amination with a substituted arylamine of the formula (V)

W—NH$_2$          (V)

wherein W is either A or B as defined in claim 1, and wherein said reductive amination is optionally performed in the presence of a solvent,
to give a compound of formula (II)

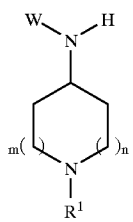

(II)

wherein $R^1$ is as defined in claim 1, m=1, and n=1, and W is either A or B as defined in claim 1; and (b) reacting the compound of formula (II) produced in step (a) with an arylating agent of the formula (III)

W—Z          (III)

wherein W is either A or B as defined in claim 1, and Z is either $Z^1$ or $Z^2$ as defined in claim 1, optionally in the presence of a catalyst to give a compound of claim 1.

73. A process for the preparation of a compound according to claim 37 comprising:
(a) subjecting a ketone of the formula (IV)

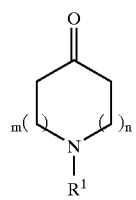

(IV)

wherein $R^1$ is as defined in claim 37, m=0, and n=1, to reductive amination with a substituted arylamine of the formula (V)

W—NH$_2$ (V)

wherein W is either A or B as defined in claim 37, and wherein said reductive amination is optionally performed in the presence of a solvent,
to give a compound of formula (II)

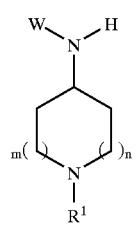

(II)

wherein $R^1$ is as defined in claim 37 m=0, and n=1, and W is either A or B as defined in claim 37; and (b) reacting the compound of formula (II) produced in step (a) with an arylating agent of the formula (III)

W—Z          (III)

wherein W is either A or B as defined in claim 37, and Z is either $Z^1$ or $Z^2$ as defined in claim 37, optionally in the presence of a catalyst to give a compound of either claim 37.

\* \* \* \* \*